(12) United States Patent
Radovic

(10) Patent No.: US 10,667,574 B2
(45) Date of Patent: Jun. 2, 2020

(54) FUNCTIONAL ORTHOTIC SUPPORT STRUCTURE FOR FOOTWEAR

(71) Applicant: Philip Andrew Radovic, San Clemente, CA (US)

(72) Inventor: Philip Andrew Radovic, San Clemente, CA (US)

(*) Notice: Subject to any disclaimer, the term of this patent is extended or adjusted under 35 U.S.C. 154(b) by 0 days.

(21) Appl. No.: 16/459,376

(22) Filed: Jul. 1, 2019

(65) Prior Publication Data

US 2019/0320758 A1  Oct. 24, 2019

Related U.S. Application Data

(63) Continuation of application No. PCT/US2019/017550, filed on Feb. 11, 2019.

(60) Provisional application No. 62/630,518, filed on Feb. 14, 2018.

(51) Int. Cl.
| | |
|---|---|
| *A43B 7/14* | (2006.01) |
| *A43B 7/22* | (2006.01) |
| *A43B 17/02* | (2006.01) |
| *A43B 3/12* | (2006.01) |
| *A43B 3/00* | (2006.01) |

(52) U.S. Cl.
CPC .............. *A43B 7/223* (2013.01); *A43B 3/128* (2013.01); *A43B 7/14* (2013.01); *A43B 7/141* (2013.01); *A43B 7/226* (2013.01); *A43B 17/023* (2013.01); *A43B 3/0073* (2013.01); *A43B 3/12* (2013.01)

(58) Field of Classification Search
CPC ........... A43B 7/14; A43B 7/141; A43B 7/142; A43B 7/223; A43B 7/226; A43B 3/12; A43B 3/128

USPC ........ 36/43, 91, 145, 166, 173, 80, 138, 11.5
See application file for complete search history.

(56) References Cited

U.S. PATENT DOCUMENTS

| | | | | |
|---|---|---|---|---|
| 855,163 | A * | 5/1907 | Cotter | A43B 7/142 36/179 |
| 1,219,257 | A * | 3/1917 | Cornet | A43B 7/142 36/177 |
| 1,544,625 | A * | 7/1925 | Austin | A43B 7/141 36/173 |
| 1,575,645 | A * | 3/1926 | Scholl | A43B 7/141 36/179 |

(Continued)

OTHER PUBLICATIONS

International Search Report & Written Opinion, dated May 7, 2019, in International Patent Application No. PCT/US2019/017550.

*Primary Examiner* — Marie D Bays
(74) *Attorney, Agent, or Firm* — Knobbe, Martens, Olson & Bear, LLP

(57) ABSTRACT

An orthotic support structure or shell may be used with footwear intrinsically or as a removable and transferable device. The footwear may be a sandal assembly including a sole, a strap and an orthotic shell. The strap is attached to the sole and configured to secure the sole against the foot. The orthotic shell is positioned within the sole and formed from a semi-rigid material. The orthotic shell includes a heel portion configured to support a heel region of the foot, and a midfoot portion connected to the heel portion and configured to support an arch region of the foot, the midfoot portion comprising an arched shank having a curved convex shape. The arched shank is configured to deflect under a downward force applied thereon which reactively rotates the heel portion toward the heel region of the foot.

20 Claims, 26 Drawing Sheets

(56) References Cited

U.S. PATENT DOCUMENTS

| | | | |
|---|---|---|---|
| 2,084,735 A * | 6/1937 | Trust Company The Cleveland | A43B 7/06 36/173 |
| 2,120,055 A * | 6/1938 | MacDonald | A43B 7/144 36/167 |
| 4,756,096 A * | 7/1988 | Meyer | A43B 7/28 12/142 N |
| 4,858,338 A * | 8/1989 | Schmid | A43B 3/0052 36/44 |
| 5,311,680 A * | 5/1994 | Comparetto | A43B 7/14 36/140 |
| 6,173,511 B1 * | 1/2001 | Perrault | A43B 7/141 36/140 |
| 6,457,261 B1 | 10/2002 | Crary | |
| 6,502,330 B1 * | 1/2003 | David | A43B 13/026 36/144 |
| 6,598,321 B2 | 7/2003 | Crane | |
| 6,886,276 B2 * | 5/2005 | Hlavac | A61F 5/14 2/240 |
| 6,915,598 B2 | 7/2005 | Grisoni | |
| 6,976,322 B1 | 12/2005 | Walker | |
| 8,042,287 B2 * | 10/2011 | Reinhardt | A43B 7/141 36/179 |
| 8,225,534 B2 | 7/2012 | Mueller | |
| 8,341,856 B2 | 1/2013 | Smith | |
| 9,398,785 B2 * | 7/2016 | Horacek | A43B 3/0036 |
| 2002/0162250 A1 * | 11/2002 | Campbell | A43B 7/141 36/166 |
| 2003/0061735 A1 * | 4/2003 | Polifroni | A43B 7/141 36/44 |
| 2003/0172548 A1 | 9/2003 | Fuerst | |
| 2004/0025376 A1 * | 2/2004 | Grisoni | A43B 7/141 36/44 |
| 2007/0234592 A1 * | 10/2007 | Crates | A43B 1/0045 36/44 |
| 2010/0018077 A1 * | 1/2010 | Marone | A43B 7/223 36/91 |
| 2010/0293811 A1 | 11/2010 | Truelsen | |
| 2014/0059895 A1 * | 3/2014 | Arciuolo | A43B 7/00 36/173 |
| 2017/0196306 A1 * | 7/2017 | Arciuolo | A43B 5/00 |

\* cited by examiner

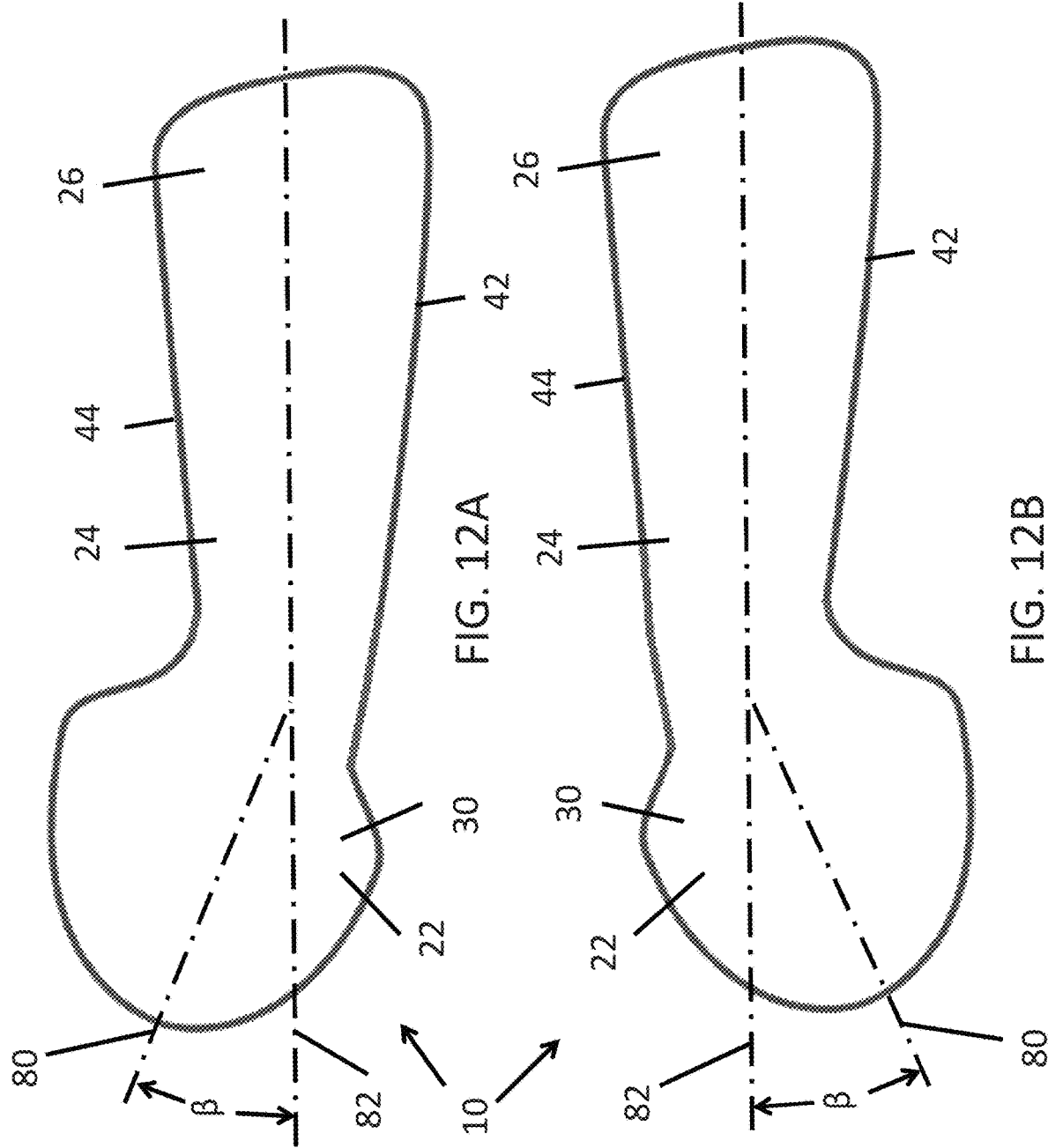

FUNCTIONAL ORTHOTIC SUPPORT STRUCTURE FOR FOOTWEAR

PRIORITY AND CROSS REFERENCE TO RELATED APPLICATIONS

This application is a Continuation Application of International Application No. PCT/US2019/017550, filed Feb. 11, 2019, which claims priority to U.S. Provisional Patent Application No. 62/630,518 filed Feb. 14, 2018, the disclosure of which is hereby incorporated by reference in its entirety herein.

BACKGROUND

Field

The present disclosure relates to an orthotic support structure, such as for example a shell, fitted to the sole of footwear, such as for example, a flip-flop style light sandal. The orthotic shell provides structure to the sole such that the sole conforms to the shape of the orthotic shell and provides orthotic foot support to a wearer of the footwear.

Description of Related Art

Flip-flop sandals are a popular and fashionable form of casual footwear due to their simple construction, low cost and minimalist aesthetics. Generally, the sole of a flip-flop is thin, flat and does not provide substantial orthotic support to the foot of the wearer. As a result, regular and prolonged wearing of flip-flops can cause short and long-term musculoskeletal damage resulting in osteoporosis, arthritis, shin splints, unstable gait, foot pain, knee pain, Achilles tendinitis, posterior tibial tendinitis, piriformis syndrome, plantar fasciitis, hip pain, lower back pain, hammertoes, bunions, stress fractures, capsulitis, metatarsalgia, subluxation syndrome, neuromas, bursitis, corns, callouses, heel fissures, peroneal tendinitis, extensor tendinitis and many other conditions.

SUMMARY

Typical footwear (e.g., sandals, shoes, boots) is designed with little or no attention to providing proper functional, mechanical and dynamic support to the wearer's foot. This is particularly true for wearers who may have abnormalities or deformities. Such problems can be addressed using functionally biomechanical orthotic inserts (also referred to as "orthotics"), which are devices placed in footwear to cooperate with the plantar surfaces of a wearer's feet to provide various levels of support and motion control to enhance comfort and/or compensate for foot abnormalities or deformities and/or prevent their development or progression.

Typically, in order to be effective, orthotics must be custom made. When generic, they are addressing over-pronation or over-supination (cavus/planus foot types), but not both and if supportive, cannot allow for "mobile adaptation". To accommodate a spectrum of structural foot types, generic orthotics are soft, insufficiently supportive, or contoured, or functional and simply act as soft "arch supports". In addition to these drawbacks, foot wear, such as sandals, with intrinsic orthotic design are challenged in providing adequate biomechanical control due to the loss of foot contact with the sandal during gait which causes abnormal compensatory biomechanics such as toe flexion/extension and/or foot abduction/adduction, hip extension/flexion, increased cadence, shortened stride and or adjusting foot strike pattern, etc.

The orthotic shell herein (interchangeably referred to herein as an "orthotic device") provides prolonged dynamic contact with the wearer's foot allowing for a more true biomechanical and adaptability control that may be applied to a wide range of footwear, including without limitation, athletic shoes, casual shoes, dress shoes, work boots and recreational footwear.

The footwear having orthotic shell described herein is configured to provide enhanced support and may compensate for various foot abnormalities or deformities in a particularly robust and durable form factor without need for adjustment or customization. The orthotic described herein is a dynamic, functional orthotic that allows the foot to function as a "mobile adapter" while adhering to biomechanical foot principles and incorporates the Spiraldynamic™ theory of foot function. It controls the heel frontal plane motion and allows for adaptable forefoot variances (varus/valgus) by accommodating the medial and lateral foot columns while supporting the transverse arch of the foot. At least one embodiment of the footwear having an orthotic insole may be summarized as a composite sole structure including an orthotic shell received between insole platform and an outsole. The orthotic shell may be completely enclosed between the insole platform and the outsole such that the orthotic shell is not externally visible when the footwear is completely assembled. The orthotic shell is preferably about two-thirds, three-quarters, four-fifths or more of an entire longitudinal length of the footwear and made of a semi-rigid material that is relatively more rigid than a material of the insole platform. The orthotic shell includes a heel portion to support a heel of a foot of a wearer and a forefoot portion to support a forefoot of the wearer at least in a region behind and near metatarsal heads of the foot and the transverse arch of the foot. The orthotic shell may be shaped to support the central three metatarsal heads in a neutral, generally horizontal position while supporting the transverse arch.

The orthotic shell may include a shank positioned between the heel cup and the metatarsal arch. In some embodiments, the shank may include a flexible extension angled at 15-30 degrees. The shank is curved in such a way as to act dynamically in during gait so as to provide a closer and more prolonged interface between the wearer's heel and the heel cup of the footwear. This allows a more natural gait and adaptable foot function particularly in a sandal due to better and prolonged contact and less need for compensatory foot/gait adjustment such as shortened stride, rearfoot instability (excessive inversion or eversion), increased cadence and toe flexion/extension and or foot adduction/abduction.

In some embodiments, the footwear includes an outsole platform and a full-length insole sandwiching an orthotic midsole. An upper or vamp in the form of retention straps are providing for holding the sandal to the foot of the wearer. The retention straps may be formed from a material featuring multi-directional stretching capability to provide enhanced comfort and durability and contact. The insoles can include tread patterns thereon to enhance traction between the sandal and a ground or other surface. The outsole platform and other components of the composite sole are sized to comfortably receive a wearer's foot of a given size (e.g., size 10 or 11). The outsole platform is preferably made of a generally flexible yet resilient, shock absorbing material, such as, for example, ethylene vinyl acetate (EVA), polyvinyl chloride (PVC), thermoplastic elastomers (TPE), rubber or similar silicone blended materials.

An orthotic midsole in the form of an orthotic shell is received between the outsole platform and the full length insole and supported in a determined orientation. The orthotic shell is preferably about two-thirds, three-quarters, four-fifths of a longitudinal length of the footwear as illustrated, however, longer or shorter orthotic shells may be used. The orthotic shell includes a heel portion to support a heel of a foot of a wearer and a forefoot portion to support a forefoot of the wearer behind and near the central three metatarsal heads of the foot. A central shank or midfoot portion extends between the heel portion and the forefoot portion. The shank portion acts in a dynamic way to allow for a more prolonged heel contact through the wearers midstance and curved to provide a similar advantage in the swing phase of the wearer's gait. The midfoot portion generally corresponds to the plantar surfaces of a typical wearer's midfoot, including, for example, an arch of the foot.

The orthotic shell is shaped such that, when it is supported at the determined orientation, the heel portion partially cups the wearer's heel to support the same in a generally vertical orientation at or near sub-talar joint neutral position. Simultaneously, the forefoot portion supports the forefoot and transverse arch such that the central three metatarsal heads are supported in a neutral, generally horizontal manner. The orthotic shell may vary in shape, thickness, flexibility, material and other aspects. It is preferably made of a material having a greater stiffness than a material of the outsole platform. Further, the orthotic shell may have a rigidity that is greater than the outsole platform which may provide shock absorption. It may be affixed between the outsole platform and full-length insole with adhesives or the like, or may be part of a midsole composite or apparatus. It may be substantially entirely enclosed between the full-length insole and the outsole platform such that the orthotic shell is not externally visible when the sandal is completely assembled and injection molded. The full-length insole covering the orthotic shell may include surface texture or design features such that the sandal has a comfortable feel when worn.

In some embodiments, the orthotic shell received in the sandal may be shaped and oriented to support the forefoot and transverse arch of the wearer relative to the heel to stabilize the forefoot in a forefoot valgus position or a forefoot varus position, rather than a neutral forefoot position. In other embodiments, a portion of the midsole platform itself may vary progressively in thickness from one side of the insole platform toward the other to simulate a forefoot valgus or forefoot varus wedge in order to allow the sub-talar joint to rest or function at or near neutral position.

The various aspects and features described above and other aspects and features described herein may be combined to provide footwear that is particularly well adapted to support the foot of a wearer in a stable manner while also allowing the foot to flex and adapt naturally during use. Although embodiments have been shown and described herein as a sandal or components for a sandal, it is appreciated that aspects and features of the embodiments may be applied to a wide range of footwear, including without limitation, athletic shoes, casual shoes, dress shoes, work boots and recreational footwear or as a removable and transferable orthotic device.

In some embodiments, a method of making footwear may include enclosing an orthotic shell between an outsole platform and an insole. The insole generally extends about an entire longitudinal length of the footwear and the orthotic shell generally extending about two-thirds, three-quarters, four-fifths or more of the entire longitudinal length of the footwear. The orthotic shell has a heel portion to support a heel of a foot of a wearer's foot, a forefoot portion to support a forefoot of the wearer's foot at least in a region behind and near the three central metatarsal heads of the foot and a midfoot dynamic "shank" portion there between and an angled sulcus extension to provide a prolonged heel contact to the wearer's foot throughout gait as well as support a midfoot of the wearer's foot. This device may reduce compensatory gait abnormalities associated with reduced foot contact to an orthotic sandal or other footwear, including without limitation, athletic shoes, casual shoes, dress shoes, work boots and recreational footwear or as a removable and transferable orthotic device.

A sandal assembly for a foot of a wearer is provided. The sandal assembly includes a sole, a strap attached to the sole and configured to secure and/or at least partially position the sole against the foot, and an orthotic shell positioned within the sole and formed from a semi-rigid material and/or a material that is more rigid than the sole. The orthotic shell includes a heel portion configured to support a heel region of the foot, and a midfoot portion connected to the heel portion and configured to support an arch region of the foot, the midfoot portion comprising an arched shank having a curved convex shape. The arched shank is configured to deflect under a downward force applied thereon which reactively rotates the heel portion toward the heel region of the foot.

In some embodiments, deflection under the downward force applied thereon increases a chord length of the arched shank in a longitudinal direction such that the increase in the chord length rotates the heel portion toward the heel region of the foot.

In some embodiments, the heel portion rotates toward and applies a force to the heel region of the foot at a midstance phase of gait.

In some embodiments, the heel portion further includes a concave heel cup. The heel can be flat "posted" to control frontal heel and/or sub-talar joint motion. The heel cup includes a base region configured to support a bottom of the heel region, and a curved concave outer sidewall region extending radially outward and upward from the base region in a direction away from the base region, the outer sidewall region configured to support an outer periphery of the heel region.

In some embodiments, the heel portion is configured to rotate between 15 degrees to 30 degrees at a heel-off phase of gait.

In some embodiments, the orthotic shell or orthotic device includes a forefoot portion connected to the midfoot portion and configured to support metatarsal heads and transverse arch of the foot.

In some embodiments, the midfoot portion and the forefoot region support the central three metatarsal of the foot.

In some embodiments, the sole includes an insole portion and an outsole portion, wherein the orthotic device is positioned between the insole and outsole portions.

In some embodiments, the orthotic device is enclosed within the sole.

In some embodiments, the orthotic device is more rigid than the sole and/or has a stiffness greater than a stiffness of the sole.

In some embodiments, the orthotic device is formed from plastic material.

In some embodiments, the orthotic device has a thickness between 1 mm to 5 mm.

In some embodiments, the orthotic device has a longitudinal length that is between one-half to four-fifths of a longitudinal length of the sole.

In some embodiments, the orthotic device has a longitudinal length that is greater than four-fifths of a longitudinal length of the sole.

In some embodiments, the orthotic device further comprises a distal extension portion connected to the forefoot portion and configured to support sulcus and plantar metatarsals of the foot.

In some embodiments, the distal extension portion is angled relative to the forefoot portion.

In some embodiments the orthotic is removable and transferable.

A sole for footwear worn on a foot of a wearer is provided. The sole includes an insole portion, an outsole portion positioned on a side of the insole portion that is opposite the foot of the wearer, an orthotic shell formed from a semi-rigid material (and/or a material that is more rigid than the sole) and positioned between the insole portion and the outsole portion. The insole can include a side configured to contact the foot of the wearer with an outsole portion positioned on another side of the insole portion that is opposite the side configured to contact the foot. The orthotic shell includes a heel portion configured to support a heel region of the foot, and a midfoot portion connected to the heel portion and configured to support an arch region of the foot, the midfoot portion comprising an arched shank having a curved convex shape. The arched shank is configured to deflect under a downward force applied thereon which reactively rotates the heel portion toward the heel region of the foot.

An orthotic device for footwear worn on a foot of a wearer is provided. The orthotic device includes a heel portion configured to support a heel region of the foot, and a midfoot portion connected to the heel portion and configured to support an arch region of the foot, the midfoot portion comprising an arched shank having a curved convex shape. The arched shank is configured to deflect under a downward force applied thereon which increases a chord length of the arched shank in a longitudinal direction. The increase in the chord length causes reactive rotation of the heel portion toward the heel region of the foot.

In some embodiments, in use, the orthotic shell is enclosed within a sole for footwear worn on a foot of a wearer.

In some embodiments, the orthotic shell is more rigid than the sole.

In some embodiments, the sole further includes an insole portion and an outsole portion, wherein the orthotic shell is positioned between the insole and outsole portions.

In some embodiments, the orthotic shell has a longitudinal length that is between one-half to four-fifths of a longitudinal length of the sole.

In some embodiments, the orthotic shell has a longitudinal length that is greater than four-fifths of a longitudinal length of the sole.

A method for manufacturing a sole that provides dynamic orthotic support to a foot of a wearer is provided. The sole has an insole portion and an outsole portion. The method includes providing a semi-rigid orthotic shell having a rigidity that is greater than the insole portion and the outsole portion, positioning the orthotic shell between the insole portion and the outsole portion, bonding the insole portion to the outsole portion such that the orthotic shell is enclosed within the sole, and conforming a shape of the insole portion according to a shape of the orthotic shell.

A method for providing dynamic orthotic support to a foot of a wearer by a sole of a footwear device fitted with a semi-rigid orthotic shell is provided. The semi-rigid orthotic shell has a rigidity that is greater than the sole. The orthotic shell includes a heel portion and a midfoot portion. The method includes applying a downward force on the midfoot portion of the orthotic shell, bending the midfoot portion in response to applying the downward force on the midfoot portion of the orthotic shell, and reactively rotating the heel portion of the orthotic shell towards the foot in response to the bending of the midfoot portion. The reactively rotating heel portion of the orthotic shell presses the sole against the foot to provide dynamic orthotic support to the foot of the wearer which is then prolonged with the forefoot loading to an angled sulcus extension. The method can include performing any of the functions and/or steps associated with the features discussed above.

A method for manufacturing an orthotic shell that provides dynamic orthotic support to a foot of a wearer is provided. The method comprises forming a concave region that is configured to support a heel region of the foot, and forming a convex region at an end of the concave region, the convex region being configured to support an arch region of the foot. The convex region is configured to deflect under a downward force applied thereon which increases a chord length of the convex region in a longitudinal direction. The increase in the chord length causes reactive rotation of the concave region toward the heel region of the foot. The method can include manufacturing any of the features discussed above.

The foregoing is a summary and contains simplifications, generalization, and omissions of detail. Those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of any subject matter described herein.

BRIEF DESCRIPTION OF THE DRAWINGS

The foregoing and other features of the present disclosure will become more fully apparent from the following description, taken in conjunction with the accompanying drawings. Understanding that these drawings depict only some embodiments in accordance with the disclosure and are, therefore, not to be considered limiting of its scope, the disclosure will be described with additional specificity and detail through use of the accompanying drawings.

FIG. 12A illustrates an embodiment of the orthotic shell in the transverse plane with the heel cup rotated toward the lateral side of the orthotic shell.

FIG. 12B illustrates an embodiment of the orthotic shell in the transverse plane with the heel cup rotated toward the medial side of the orthotic shell.

DETAILED DESCRIPTION

Figure 1:
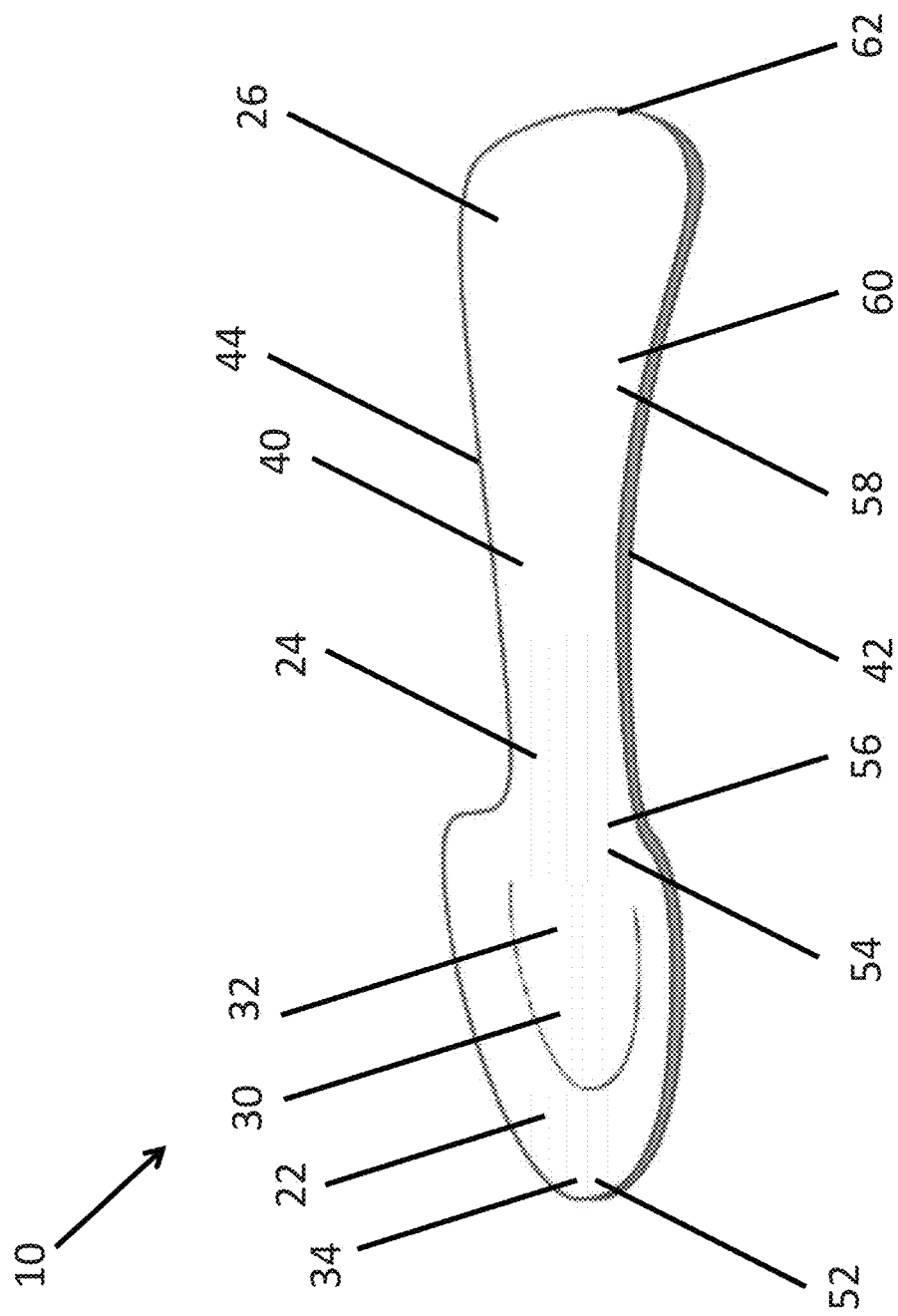
FIG. 1 is a perspective view of an example embodiment of a left orthotic shell.

In the following detailed description, reference is made to the accompanying drawings, which form a part hereof. In the drawings, similar symbols typically identify similar components, unless context dictates otherwise. The illustrative embodiments described in the detailed description and drawings are not meant to be limiting. Other embodiments may be utilized, and other changes may be made, without departing from the spirit or scope of the subject matter presented here. It will be readily understood that the aspects of the present disclosure, as generally described herein, and illustrated in the figures, may be arranged, substituted, combined, and designed in a wide variety of different configurations, all of which are explicitly contemplated and made a part of this disclosure Civilizations throughout the world have used flip-flop style light sandals as a simple and convenient form of footwear. In recent years, flip-flops such as those manufactured by, for example, Havaianas™, Ipanemas™ and Old Navy™ have become one of the most popular forms of casual footwear. As a result, flip-flops have transcended beyond pool- and beach-appropriate footwear and have become a fashionable form of footwear for casual everyday use. In warmer climate regions, flip-flops are now the most common form of footwear.

Figure 4A:
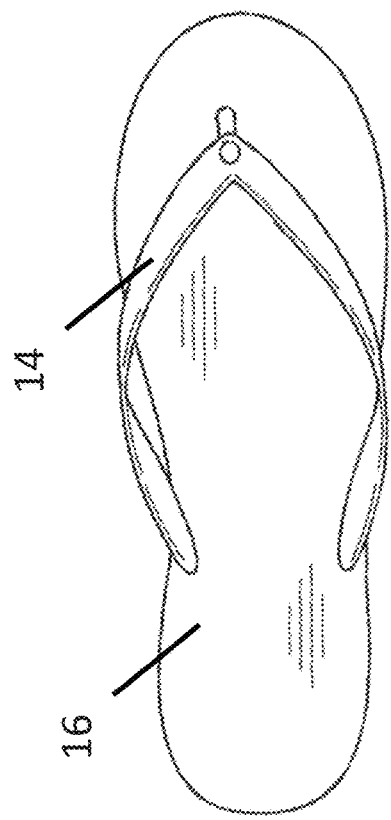
FIG. 4A is a perspective view of footwear without an orthotic shell installed.
Figure 4B:
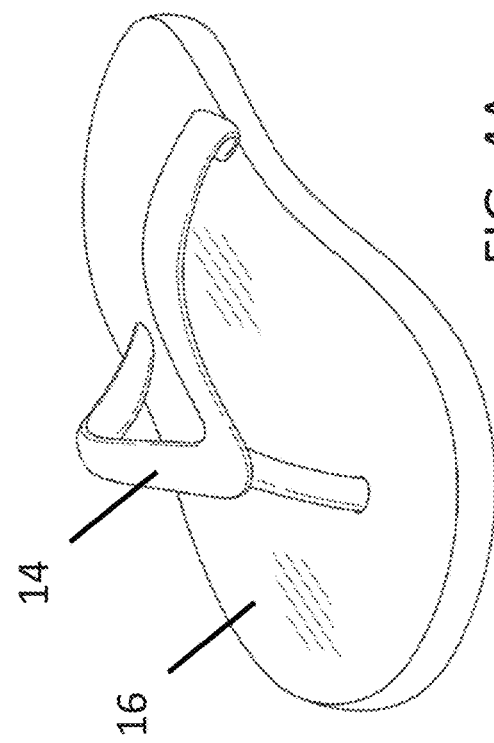
FIG. 4B illustrates the footwear in the transverse plane without an orthotic shell installed.
Figure 4C:
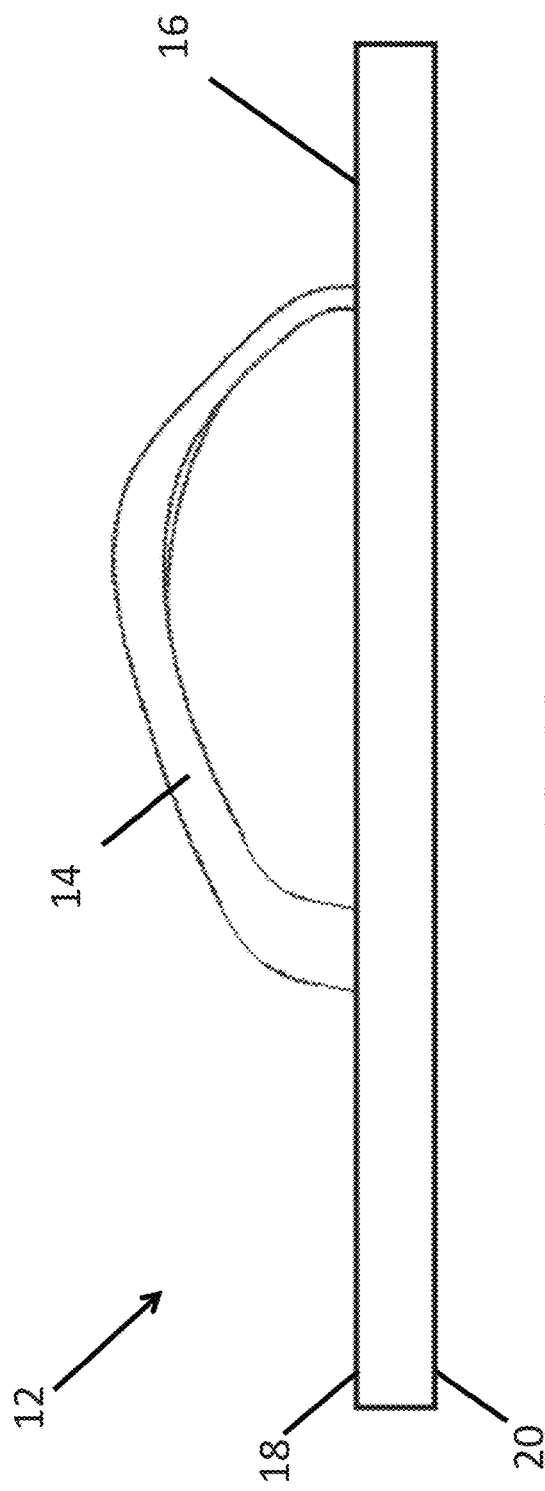
FIG. 4C illustrates the footwear in the sagittal plane without an orthotic shell installed.

Flip-flops have a simple design that is typically comprised of very few components. For example, as shown in FIGS. 4A-4C, shoes or footwear 12, such as a flip-flop sandal as illustrated as an embodiment, may comprise a thong or Y-shaped strap 14 that is anchored to a molded flat sole 16. Typically, the sole 16 is formed from rubber, PVC, leather or EVA foam. The Y-shaped strap is positioned between the first and second toes and the flip-flop is held loosely onto the foot. Due to their simple design, flip-flops are inexpensive to manufacture relative to other forms of footwear, which further expands their appeal worldwide.

As a consequence of their simple design, flip-flops typically fail to provide adequate orthotic support and stability to the wearer's feet. That is, the soles of flip-flops are typically flat and therefore fail to provide adequate heel and arch support, if any. As a result, flip-flop wearers may suffer muscular and skeletal ailments to their lower extremities (e.g., foot, ankle, knees, etc.) such as, for example, plantar fasciitis, gait issues, arthritis, lower back pain and sciatica.

Figure 12C:
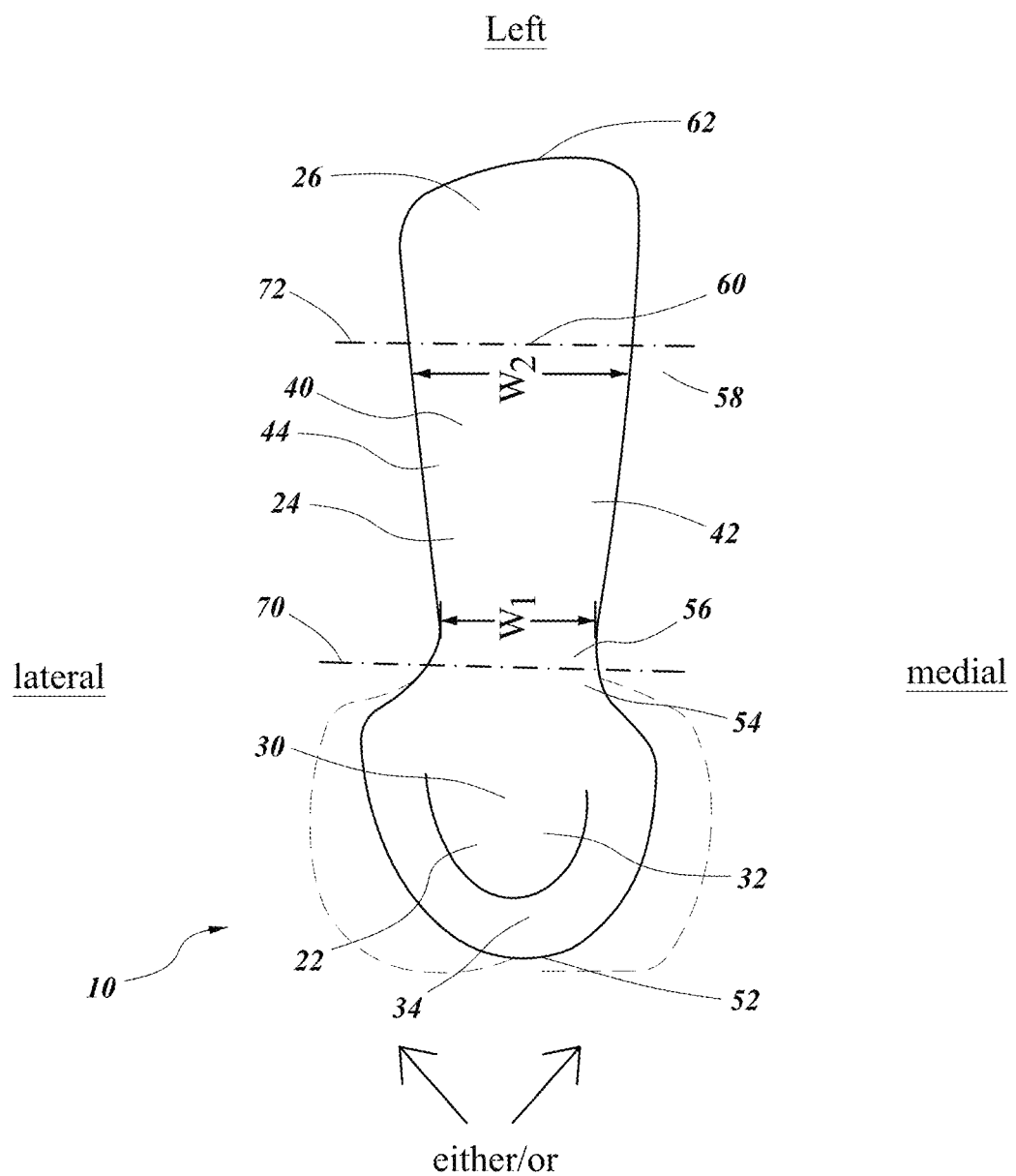
FIG. 12C illustrates an embodiment of the orthotic shell in the transverse plane with the heel cup rotated either toward the medial side or toward the lateral side of the orthotic shell.
Figure 13:
FIG. 13 illustrates dorsiflexion and plantarflexion of the ankle versus the neutral position of the ankle.

Flip-flops are typically worn loosely on the foot, which allow them to be quickly and easily donned and doffed. However, loose fitment of flip-flop also causes the toes to reactively prevent the flip-flop from falling of the foot during the swing phase of gait. That is, when a flip-flop dangles freely from the top of a foot during the swing phase of gait, the wearer typically curls his/her toes to grasp and hold the center post of the Y-shaped strap to ensure that the flip-flop does not fall off the foot. Over time, the repeated grasping and curling of the toes may cause hammertoes, neuromas, contraction deformities and bunions. Further, the wearer may also shorten his/her stride and experience excessive ankle plantarflexion or dorsiflexion. For reference, FIGS. 12A-12C illustrate ankle dorsiflexion 150 and plantarflexion 152 of the foot 2 versus the neutral position 144 of the foot 2.

Enhanced flip-flops have been developed to address the inadequacies of thin flat-soled flip-flops. Enhanced flip-flops provide a thicker, multi-density and ergonomically contoured sole that is intended to overcome the lack of support provided by flip-flops. The ergonomically contoured sole is shaped to provide increased heel and arch support, relative to a thin flat-soled flip-flop. Additionally, enhanced flip-flops may include additional heel straps that fasten the heel to the flip-flop to prevent separation of the heel and the heel portion of the sole. Further, enhanced flip-flops are typically much heavier than or relative to flat-soled flip-flops which then adds to the adverse effects during swing phase of gait.

Generally, enhanced flip-flops improve the biomechanics of thin flat-soled flip-flops by providing increased cushioning and orthotic support. However, enhanced flip-flops may cost five to ten times more than flat-soled flip-flops and still not provide the features and functionality disclosed herein. Further, the thicker contoured sole and additional straps of enhanced flip-flops provide a bulky and complicated aesthetic that is in stark contrast with the fashionable minimalistic aesthetic provided by the flat-soled flip-flops. Therefore, a need exists for a means for providing improved biomechanics to thin flat-soled flip-flops that can exceed even that of enhanced sandals and benefit various foot types.

Figure 2:
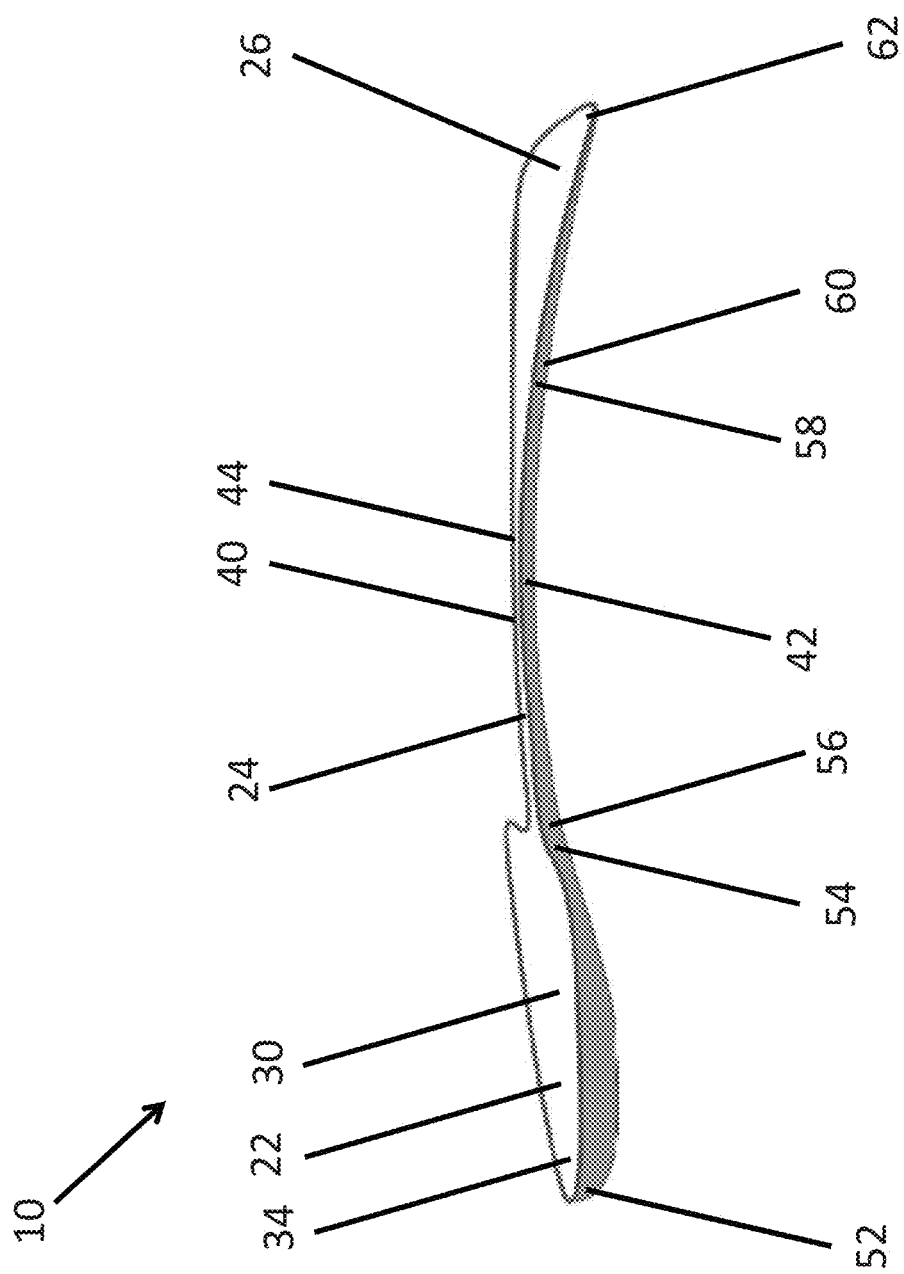
FIG. 2 illustrates an embodiment of a left orthotic shell in the sagittal plane.
Figure 3:
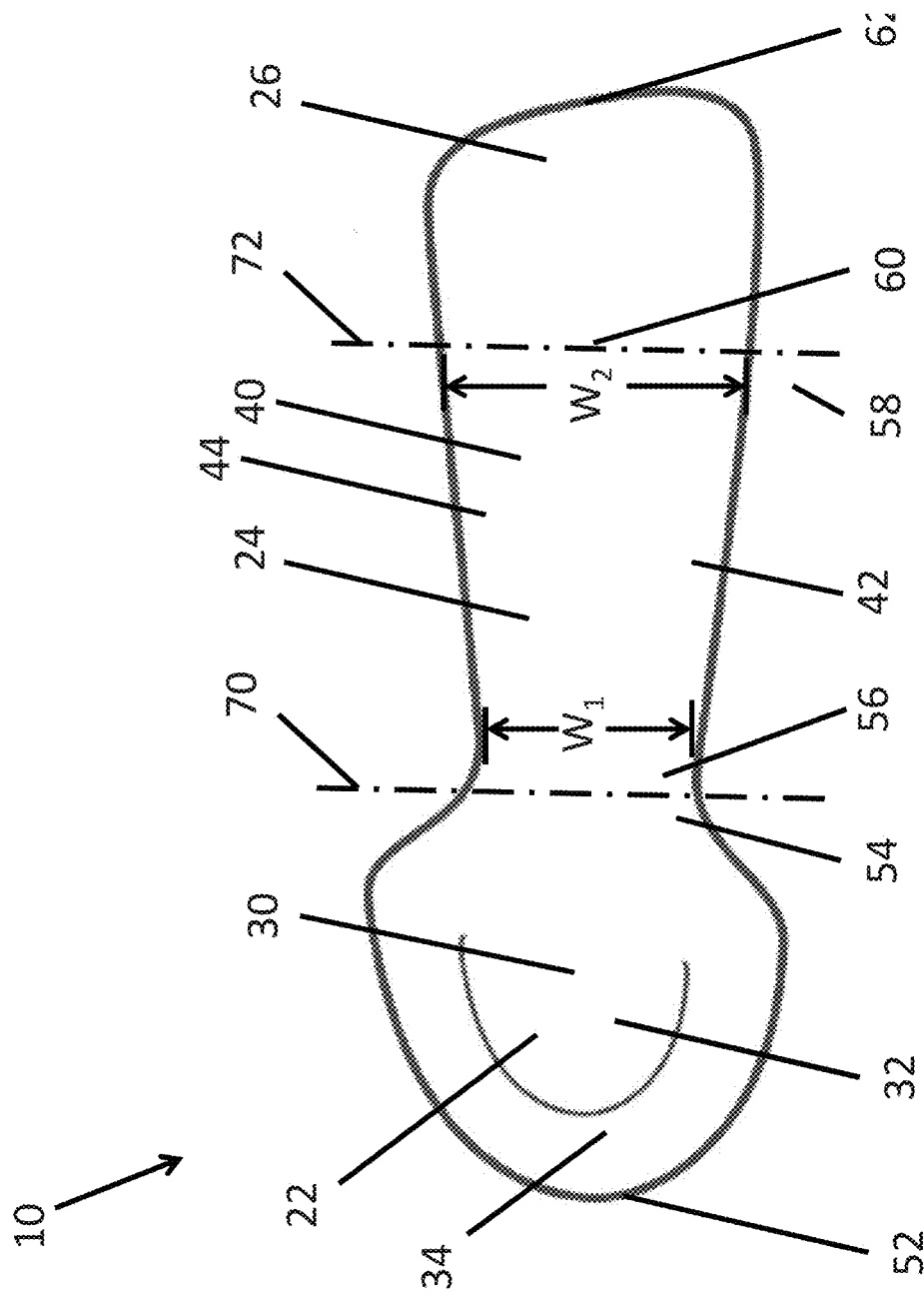
FIG. 3 illustrates an embodiment of a left orthotic shell in the transverse plane.

FIGS. 1-3 illustrates an orthotic support structure, case, frame, framework, insert, insole, midsole, device or shell 10 of the present disclosure. In use, the orthotic device or shell 10 is fitted within the sole 16 of the shoe or footwear 12, such as a thin flat-soled flip-flop, as shown in FIGS. 5-10. While this disclosure is discussed in the context of a flip-flop sandal, features of the orthotic shell 10 may be applied and used in other footwear, including other open type footwear or closed type footwear, such as sandals, slip-on type shoes, booties, sneakers, etc. As will be described in further detail below, when fitted with the orthotic shell 10, the sole 16 of the footwear 12 conforms substantially to the contoured shape of the orthotic shell 10 such that the sole 16 provides orthotic support to the foot at the initial contact (e.g., heel-strike) through midstance (e.g., foot-flat) phases of gate while allowing the foot mobile adaptability of the medial and lateral columns of the foot. Further, the orthotic shell 10 causes the sole 16 to dynamically and reactively bend and deflect under load such that the sole 16 actively supports the foot at the terminal stance (e.g., heel-off) phase of gate. Accordingly, the orthotic shell 10 may be used in any type of shoe where orthotic support to the foot at the initial contact (e.g., heel-strike) through midstance (e.g., foot-flat) phases of gate and prolonging the contact with dynamic deflection with a distal extension angled at the plantar metatarsal head and sulcus region of the foot can be beneficial. For example, while not limited to, footwear that is lightweight and/or has a sole conformed to the orthotic shell 10 where extended heel support is desired as discussed herein can be used with the orthotic shell 10.

The shank is arched lateral to medial to the contour of the transverse arch. The medial arch is slightly higher than the lateral to contour to the foot.

The distal shank is longer on the medial side to conform to the metatarsal head parabola of the foot.

Figure 5:
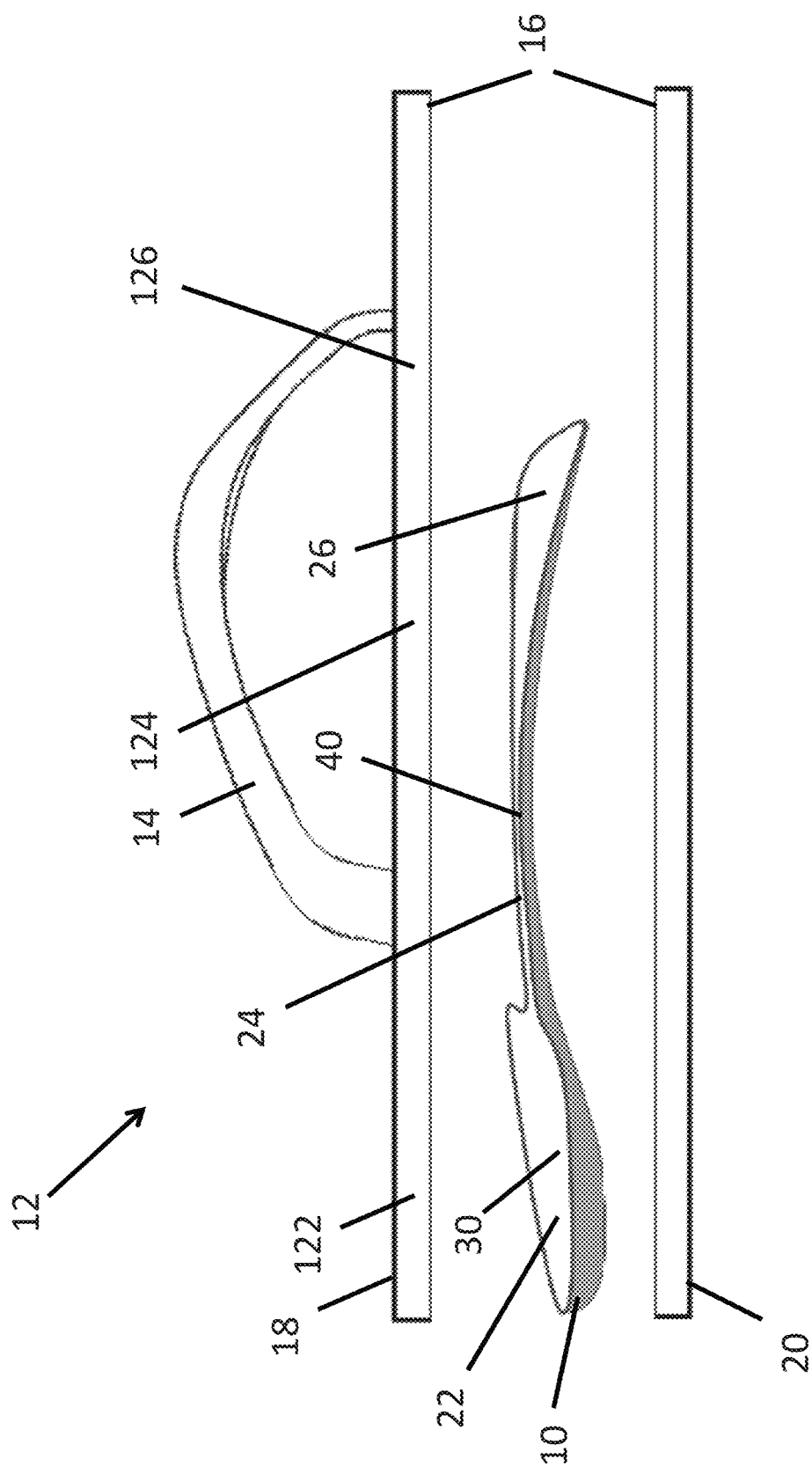
FIG. 5 is an exploded view illustrating an embodiment of a left orthotic shell in the sagittal plane positioned between an insole portion and an outsole portion of the footwear of FIGS. 4A-4C.
Figure 6:
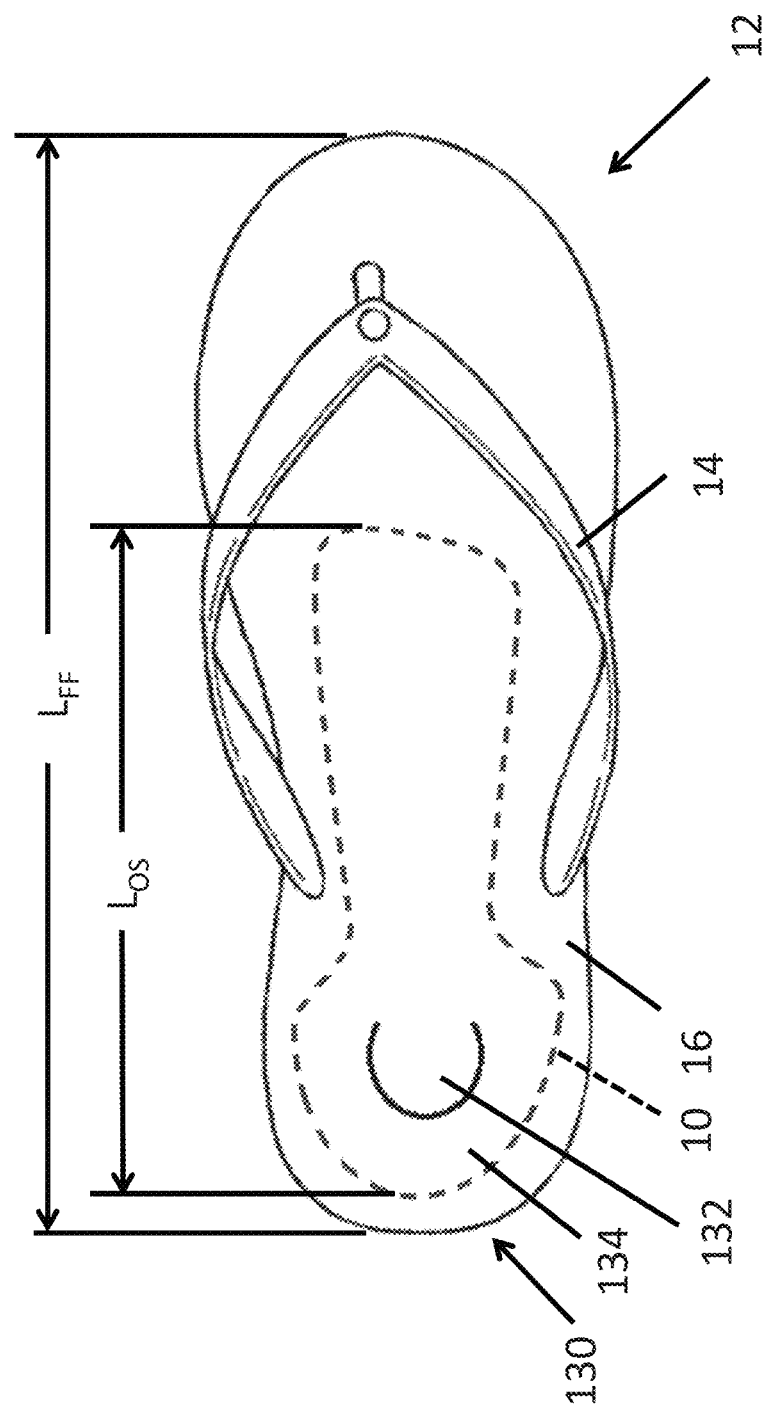
FIG. 6 illustrates the footwear in the transverse plane fitted with an embodiment of the orthotic shell to illustrate the position of the orthotic shell relative to the sole.

As illustrated in FIGS. 5 and 6, the orthotic shell 10 has a longitudinal length that is roughly four-fifths of the length of an entire longitudinal length of the sole 16 of the flip-flop 12. That is, as shown, the orthotic shell 10 has a length $L_{OS}$ and the sole 16 of the flip-flop 12 has a length $L_{FF}$. In some embodiments, the length $L_{OS}$ may be roughly four-fifths of the length $L_{FF}$. In some embodiments, the orthotic shell 10 may have a longitudinal length that is one-half to four-fifths of the length of an entire longitudinal length of the sole 16, including the foregoing values and ranges bordering therein. In other embodiments, the orthotic shell 10 may have a longitudinal length that is less than one-half (e.g., one-third to one-half) or greater than four-fifths (e.g., four-fifths to a full length) of the length of an entire longitudinal length of the sole 16, including the foregoing values and ranges bordering therein.

When fitted within the sole 16, the orthotic shell 10 supports the foot from the calcaneus (e.g., heel bone region) to a region near the metatarsal heads. In some embodiments, the orthotic shell 10 extends to a region at or rearwards of the metatarsal heads. That is, the phalanges of the foot are not supported by the orthotic shell 10. In other embodiments, the orthotic shell 10 extends to a region forward of the metatarsal heads. The orthotic shell 10 may vary in longitudinal length depending on the length of the flip-flop 12 such that orthotic shell 10 accommodates various flip-flop sizes and foot proportions. Similarly, the orthotic shell 10 may vary in lateral width depending on the width of the flip-flop 12 such that orthotic shell 10 accommodates widths for men, women and children.

The orthotic shell 10 is formed from a semi-rigid material such as, for example but not limited to, plastic, resin or reinforced composite materials. The orthotic shell 10 may be formed by molding or forming techniques such as, but not limited to, injection molding, thermoforming, vacuum forming, milling, 3D printing, etc. In some embodiments, the orthotic shell 10 is formed from polypropylene or polyethylene with a uniform thickness of 2 mm to 3 mm (millimeter(s) (mm)) substantially throughout its longitudinal length and lateral width, including the foregoing values and ranges bordering therein. In other embodiments, the orthotic shell 10 may have a thickness less than 2 mm (e.g., 1 to 2 mm) or greater than 3 mm (e.g., 3 to 4 mm).

Preferably, the orthotic shell 10 is relatively more rigid than the sole 16 of the flip-flop 12 such that the sole 16 of the flip-flop 12 conforms substantially to the contoured shape of the orthotic shell 10. In some embodiments, the sole 16 may comprise multiple layers such as an insole portion and an outsole portion. The orthotic shell 10 may be more rigid than both the insole portion 18 and the outsole portion 20. In some embodiments, the orthotic shell 10 may be more rigid than at least one of the insole portion 18 or the outsole portion 20. In some embodiments, the orthotic shell 10 may be more rigid than at least one layer or portion of the insole portion 18 and/or the outsole portion 20. It should be understood to one of ordinary skill in the art that the rigidity of the orthotic shell 10 and the sole 16 may vary relative to other portions of each of the orthotic shell 10 and the sole 16 and/or to each other such that the orthotic support provides the desired orthotic support to the foot of the wearer.

In some embodiments, the orthotic shell 10 is formed from a material that has an elastic modulus greater than the material used to form the sole 16. For example, typically, the sole of flip-flops is formed from EVA foam. Accordingly, in some embodiments, the orthotic shell 10 is formed from a material that has an elastic modulus greater than EVA foam.

Overview

With reference to FIG. 1-3, the orthotic shell 10 is comprised of a heel portion 22, a midfoot portion 24 and a forefoot portion 26. The heel portion 22 is configured to support the heel region of the foot. The midfoot portion 24 is configured to support the midfoot region of the foot. The forefoot portion 26 is configured to support the forefoot region of the foot. The total construct supports the heel, midfoot, transverse arch and medial arch while allowing for medial and lateral column adaptation.

The heel portion 22 comprises a rear portion 52 and a front portion 54. The heel portion 22 is attached to an end of the midfoot portion 24 that is opposite the forefoot portion 26. That is, the front portion 54 of the heel portion 22 is connected to a rear portion 56 of the midfoot portion 24. FIG. 3 illustrates an approximate boundary line 70 between the front portion 54 of the heel portion 22 and the rear portion 56 of the midfoot portion 24 along which the heel portion 22 and the midfoot portion 24 are connected. The heel portion 22 comprises a heel cup 30 that supports the heel region of the foot. As shown, the heel cup 30 has a concave shape that corresponds to the rounded shape of the heel of the foot. The heel cup 30 may comprise a substantially flat or planar center base region 32 that is surrounded by a curved concave outer sidewall region 34 that extends radially outward and upward in a direction away from the sole of the flip-flop. That is, the outer sidewall region 34 extends outward and upward from the base region 32 of the heel cup 30 toward the heel of user. The base region 32 is configured to support the bottom or base of the heel (i.e., the heel bone region of the foot). The outer sidewall region 34 is configured to support the outer periphery of the heel region during the stance phases of gate. The outer sidewall region 34 also aligns the heel portion 22 as it receives the heel upon the heel-strike phase of gait such that orthotic shell 10 is substantially aligned with the foot prior to the stance phases of gate.

The midfoot portion 24 comprises a rear portion 56 and a front portion 58. The rear portion 56 of the midfoot portion 24 is attached to the front portion 54 of the heel portion 22 which may be angled 15-45 degrees in the sagittal plane, and to the front portion 58 is attached to a rear portion 60 of the forefoot portion 26.

The midfoot portion 24 comprises an arched shank 40 that extends between the heel portion 22 and the forefoot portion 26. The arched shank 40 has a curved convex shape from lateral to medial and distal to proximal that corresponds to and supports the plantar surfaces of the foot including, for example, the metatarsals and transverse arch of the foot. A rear portion 56 of the midfoot portion 24 is connected to a front portion 54 of the heel cup 30. In some embodiments, the arched shank 40 is connected to the base region 32 at an inflection point between the convex curvature of the arched shank 40 and the concave curvature of the base region 32. It is at this point where the heel portion is angled 15-45 degrees to the proximal shank portion. As shown in FIG. 2 (see also FIG. 3), the convex arch may be higher on a medial side 42 than on a lateral side 44 of the arched shank 40 in substantial conformity with the medial and lateral longitudinal arches of the foot. That is, the height of the convex arch on a medial side 42 may be greater than the height of the convex arch on a lateral side 44. In some embodiments, the lateral side 44 of the arched shank 40 may be substantially flat.

As shown in FIG. 3, the midfoot portion 24 varies in lateral width along its longitudinal length. The width of the arched shank 40 is narrower at an end adjacent to the heel cup 30 and increases along its length toward the forefoot portion 26. The rear portion 56 of the midfoot portion 24 may have a width $W_1$ that increases to a width $W_2$ at the front portion 58 of the midfoot portion 24. The arched shank 40 expands in width such that the three central metatarsal of the foot are supported along their length by midfoot portion 24. In some embodiments, the width $W_1$ of the arched shank 40 at the rear portion 56 of the midfoot portion 24 may be substantially similar to the width of the base region 32. In some embodiments, the width $W_2$ of the arched shank 40 at the front portion 58 of the midfoot portion 24 may be substantially similar to the width of the rear portion 56 of the forefoot portion 26.

The forefoot portion 26 comprises a rear portion 60 and a front portion 62. The rear portion 60 of the forefoot portion 26 is attached to the front portion 58 of the midfoot portion 24. FIG. 3 illustrates an approximate boundary line 72 between the front portion 58 of the midfoot portion 24 and the rear portion 60 of the forefoot portion 26 along which the midfoot portion 24 and the forefoot portion 26 are connected. The front portion 62 defines an end of the orthotic shell 10.

The forefoot portion 26 supports the forefoot region of the foot such that the central three metatarsal are supported along their length and in the transverse arch. The forefoot portion 26 extends to a region near the three central metatarsal heads of the foot and may extend to a position rearward, at or forward of the three central metatarsal heads. In some embodiments, the forefoot portion 26 supports the central three metatarsal heads in a neutral, generally horizontal position. In other embodiments, the forefoot portion 26 may support the central three metatarsal in a forefoot valgus position or a forefoot varus position, rather than a neutral forefoot position. Further, with the forefoot portion 26 supporting the three central metatarsals, the orthotic shell 10 can accommodate foot deformities, such as forefoot valgus and forefoot varus, while still achieving the features and functionality of the orthotic shell 10 as discussed herein by not relying on contact or pressure from the outer metatarsals and allowing them to "float". This can be further accommodated by the rotational flexibility of the shank portion in the frontal plane. This can neutralize/accommodate forefoot to rearfoot varus/valgus deformities and allow for normal mobile adaptability. In some embodiments, the midfoot portion 24 and/or forefoot portion 26 may be shaped to support the three central metatarsal and one or both outer metatarsals. In other embodiments, the midfoot portion 24 and/or forefoot portion 26 may be shaped to support any combination of metatarsals in the foot.

In some embodiments, the orthotic shell 10 received in the footwear 12 may be shaped and oriented to support the forefoot of the wearer relative to the heel to stabilize the forefoot in a forefoot valgus position or a forefoot varus position, rather than a neutral forefoot position. In other embodiments, a portion of the midsole platform itself may vary progressively in thickness from one side of the insole platform toward the other to simulate a forefoot valgus or forefoot varus wedge.

Fitting of Orthotic Shell to Sole

FIGS. 4A-4C illustrate an exemplary thin flat-soled flip-flop 12 with a flat non-contoured sole 16. As illustrated in FIG. 4C, the sole 16 of the flip-flop 12 is comprised of an insole portion 18 and an outsole portion 20. The insole portion 18 faces and contacts the foot and the outsole portion 20 faces and contacts the ground. In some embodiments, the sole 16 may be unitary and formed from a material such as, for example, EVA foam. In some embodiments, the sole 16 may comprise as assembly of a plurality of layers of foam, fabric and rubber.

FIG. 5 illustrates the flat-soled flip-flop 12 and the orthotic shell 10 in the sagittal plane 158. As shown, the orthotic shell 10 is positioned between the insole portion 18 and the outsole portion 20. The heel cup 30 of the orthotic shell 10 is positioned within and aligned with the heel portion 122 of the flip-flop 12 such that the heel is received and supported by the heel cup 30. The arched shank 40 is positioned within the midfoot region 124 of the flip-flop 12 such that the central three metatarsals are supported along their length by the arched shank 40. The forefoot portion 26 is positioned within the forefoot region 126 of the flip-flop 12 such that the central three metatarsal heads are supported by the forefoot portion 26 in a neutral, generally horizontal position while contouring support of the transverse arch.

During assembly, in some embodiments, the orthotic shell 10 is positioned between the insole portion 18 and the outsole portion 20 which are then bonded together such that the orthotic shell 10 is sandwiched between the insole portion 18 and the outsole portion 20. The sole 16 may be assembled by bonding together the insole portion 18 the outsole portion 20 by any mechanical means such as, but not limited to, adhesives, stitching, bonding, fasteners, etc. As a result, the orthotic shell 10 is retained between the insole portion 18 and the outsole portion 20 and held within the sole 16. When the insole portion 18 is bonded to the outsole portion 20, the orthotic shell 10 may be completely enclosed or substantially completely enclosed such that the orthotic shell 10 is not externally visible when the sole 16 is fully assembled, as illustrated in FIGS. 6 and 7.

Figure 7:
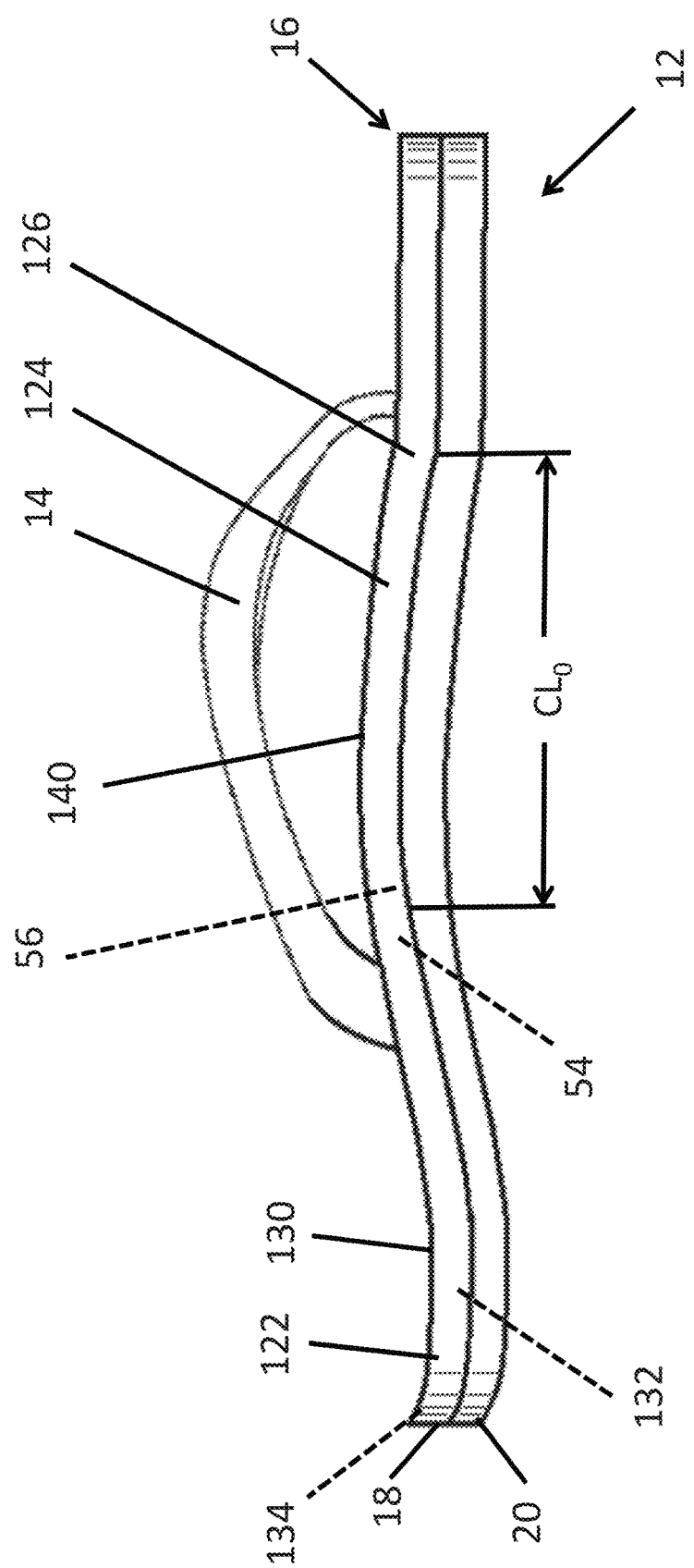
FIG. 7 illustrates the footwear fitted in the sagittal plane with an embodiment of the orthotic shell to illustrate the shape and contour of the sole.

FIG. 7 illustrates the flip-flop 12 in the sagittal plane 158 after the orthotic shell 20 has been fitted to the sole 16. In contrast to FIG. 4C which illustrates the sole 16 prior to fitting of the orthotic shell 10, the sole 16 illustrated in FIG. 7 has a shape and contour that corresponds to and matches that of the orthotic shell 10. As shown in FIG. 7, the heel portion 122, the midfoot portion 124 and the forefoot portion 126 substantially conform to the shape and contours of the heel portion 22, the midfoot portion 24 and the forefoot portion 26 of the orthotic shell 10. Similarly, the sole 16 also comprises a heel cup 130 and a midfoot arch region 140 that substantially conform to the shape and contours of the heel cup 30 and the midfoot arch shank 40 of the orthotic shell 10. That is, the heel cup 130 has a concave shape that corresponds to the rounded shape of the heel region 4 of the foot 2. Similar to the orthotic shell 10, the heel cup 130 may comprise a substantially flat or planar center base region 132 that is surrounded by a curved outer sidewall region 134 that extends and rises from the base region 132. The arch region 140 has a curved convex shape that corresponds to and supports the plantar surfaces of the foot including, for example, the metatarsals and transverse arch of the foot.

The insole and outsole portions 18, 20 substantially conform to the shape of the orthotic shell 10 because the orthotic shell 10 has a rigidity and/or stiffness greater than the sole 16. Accordingly, the insole and outsole portions 18, 20, which are relatively more flexible than the orthotic shell 10, follow the contours of the less flexible orthotic shell 10. As a result, the orthotic shell 10 provides an internal frame, structure or backbone that shapes the insole and outsole portions 18, 20.

Orthotic Support at Initial Contact and Midstance

Figure 8:
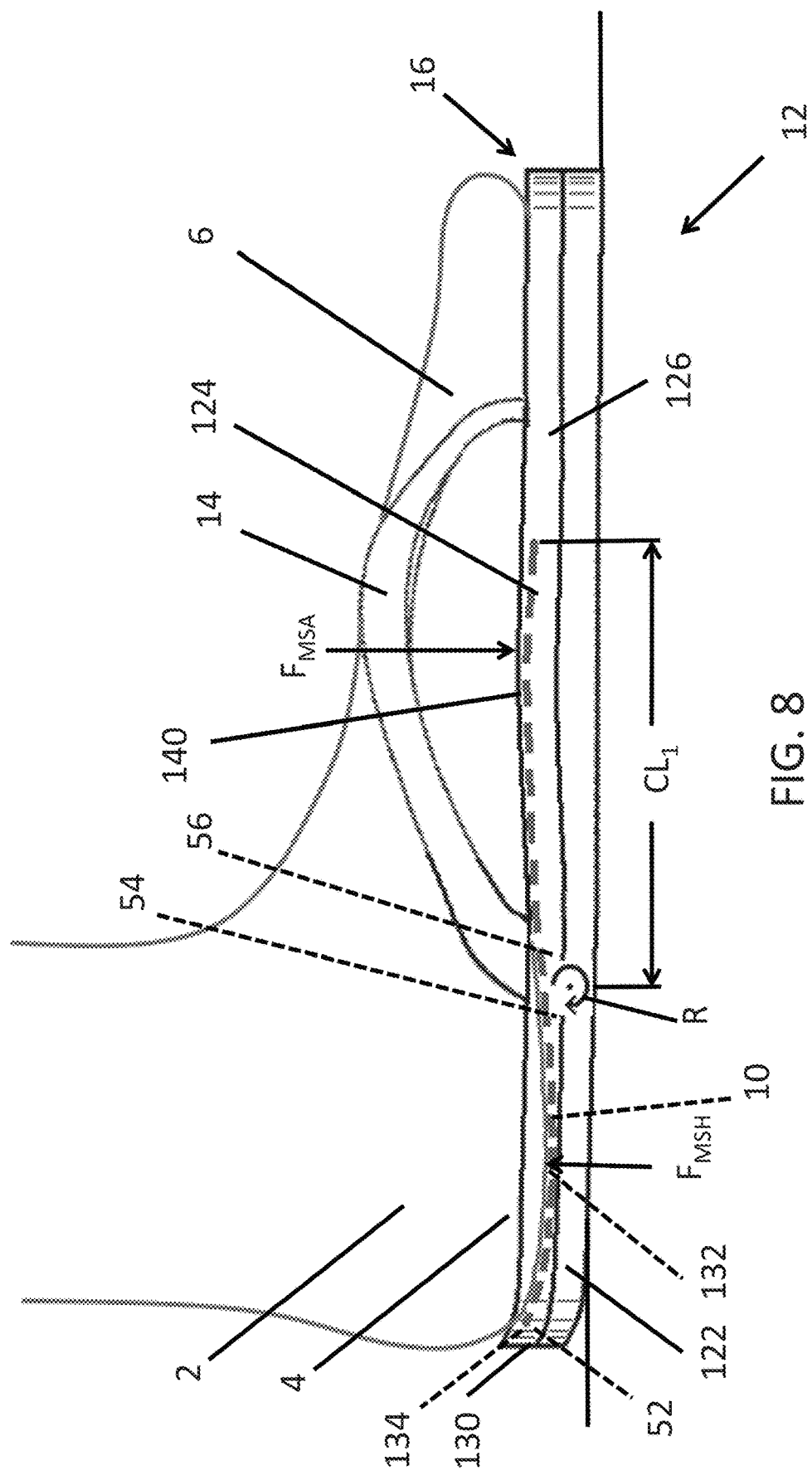
FIG. 8 illustrates the footwear in the sagittal plane fitted with an embodiment of the orthotic shell to illustrate the orthotic support provided by the sole at the midstance phase of a wearer's gait.

FIG. 8 illustrates the flip-flop 12 fitted with and conforming to the shape of the orthotic shell 10. The flip-flop 12 is donned on a wearer's foot 2 at the midstance (foot-flat) phase of gait. As shown, the sole 16 fitted with the orthotic shell 10 which provides orthotic support to the heel region 4 and the midfoot region 6 of the foot 2. The heel region 4 of the foot 2 contacts and is supported by the heel cup 130 of the sole 16. The midfoot region 6 of the foot 2 contacts and is supported by the arch region 140 of the sole 16.

Similar to the orthotic shell 10, the heel cup 130 of the sole 16 receives the heel region 4 of the foot 2 such that the outer periphery of the heel region 4 is substantially cupped and cradled by the heel cup 130 at the initial contact (heel-strike) through the midstance (foot-flat) phases of gate. At the initial contact (heel-strike) phase of gait, the curved outer sidewall region 134 of the heel cup 130 may initially engage the outer periphery of the heel region 4 as the heel region 4 is approaching the sole 16 upon heel-strike. As the contact with the outer periphery of the heel region 4 increases upon initial contact (heel-strike), the curved outer sidewall region 134 increasingly aligns the heel cup 130 with the heel region 4 of the foot 2 such that heel region 4 is centered with the sole 16 as the heel region 4 is seated within the heel cup 130 at midstance (foot-flat).

Figure 14:
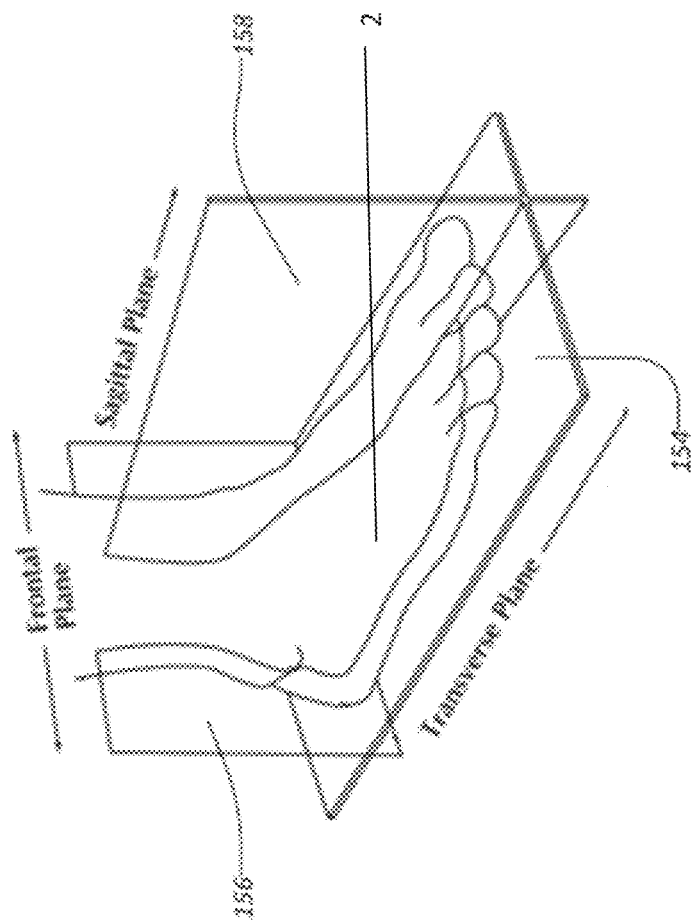
FIG. 14 illustrates an example embodiment of the transverse, frontal and sagittal planes.

The cradling and cupping of the heel region 4 of the foot 2 supports the outer periphery of the heel region 4 in the frontal (coronal), transverse and sagittal planes. For reference, FIG. 14 illustrates the foot 2 with respect to the transverse plane 154, the frontal plane 156, and the sagittal plane 158. Supporting the heel region 4 in the transverse plane 154, the frontal plane 156, and the sagittal plane 158 may promote healthy biomechanics of the wearer's foot and ankles. For example, supporting the heel region 4 in the transverse plane 154, the frontal plane 156, and the sagittal plane 158 may promote neutral alignment of the foot 2 and aid in preventing, inhibiting or mitigating under pronation (supination) and over pronation.

Figure 16:
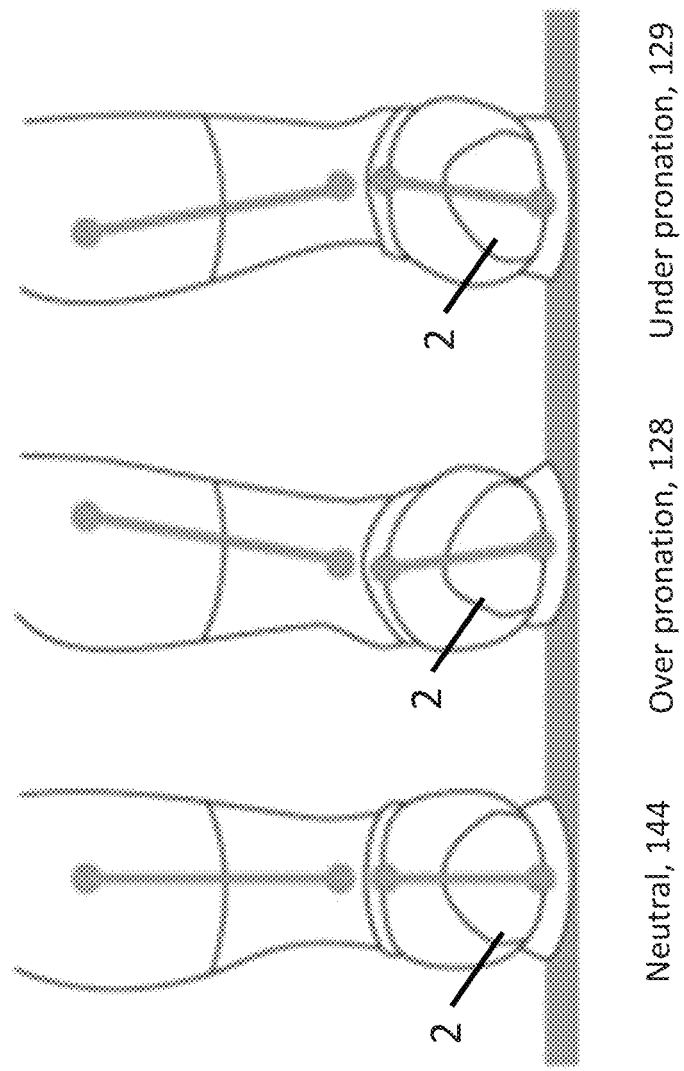
FIG. 16 illustrates rotation or inversion/eversion movement of the foot and/or leg in the frontal plane. Right foot from posterior.

As discussed herein and with reference to FIG. 16, over pronation 128 and under pronation 129 can refer to rotation of the foot 2 so that in the corresponding anatomical position, the sole of the foot 2 is facing anteriorly (inverted) or posteriorly (everted). FIG. 14 illustrates the foot 2 with respect to the frontal plane 156 in a neutral position 144, over pronation/everted 128 and under pronation/inverted 129.

The cradling and cupping of the heel region 4 may also maintain alignment of the heel portion 122 of the sole 16 with the heel region 4 of the foot 2 upon each step of the wearer. Proper alignment of the foot 2 with the sole 16 in the transverse plane 154, the frontal plane 156, and the sagittal plane 158 may improve the fitment, comfort and aesthetic of the flip-flop 12.

The arch region 140 of the sole 16 supports the midfoot region 6 of the foot 2. Similar to the orthotic shell 10, the arch region 140 has a curved convex shape that corresponds to and supports the plantar surfaces of the foot including, for example, the metatarsals and transverse arch of the foot 2. Support of the metatarsals and transverse arch may prevent collapse of the arch and flat-footedness and promote interlocking of the tarsal-metatarsal joint complex. This along with controlling frontal plane heel/sub-talar joint motion allows locking of the mid-tarsal joint so the foot can function as a rigid lever in propulsion. Providing arch support as well as this biomechanical foot control may also alleviate or prevent plantar fasciitis and a multitude of the aforementioned lower extremity ailments and improve the comfort of the flip-flop 12

Further, as shown in FIG. 8, the midfoot region 6 of the foot 2 applies a substantially downward midstance arch force $F_{MSA}$ onto the arch region 140 of the sole 16 during midstance (foot-flat). As previously described, the arch region 140 of the sole 16 is supported by the semi-rigid arch shank 40 of the orthotic shell 10 within the sole 16. Accordingly, the midstance arch force $F_{MSA}$ causes the convex arch shank 40 and the convex arch region 140 to flatten such that the height of the contour and/or the amount of convexity of both the arch shank 40 and the arch region 140 decreases when compared to an unloaded state of the sole 16, as shown in FIG. 7. That is, the convex arch shank 40 is compressed between the wearer's foot (i.e., which is applying the midstance arch force $F_{MSA}$) and the surface on which the sole 16 is contacting (e.g., the ground) such that the convex arch region 140 deforms and bends which decreases the convexity of the convex arch region 140. In some embodiments, the arched shank 40 and the convex arch region 140 retain a degree of convexity such that arch support is provided by the sole 16 at midstance (foot-flat). That is, in some embodiments, the convex curvature of the arched shank 40 and the arch region 140 are not entirely flattened at midstance (foot-flat). The degree of convexity may be varied according to the material stiffness, rigidity, geometry and/or construction of each of the orthotic shell 10 and sole 16.

As the convex curvature of the arch region 140 flattens and compresses under the midstance arch force $F_{MSA}$, the chord length of the convex curvature of the arch region 140 in the longitudinal direction increases from a chord length $CL_0$ in the unloaded state (shown in FIG. 7) to $CL_1$ in the midstance loaded state (shown in FIG. 8). In some configurations, the difference in length between $CL_1$ and $CL_0$ may be between 1 mm to 5 mm, including the foregoing values and ranges bordering therein. In other embodiments, the difference in length between $CL_1$ and $CL_0$ may be less than 1 mm or greater than 5 mm, including the foregoing values and ranges bordering therein.

As previously described, the rear portion 56 of the arched shank 40 is connected to the front portion 54 of the heel cup 30. Therefore, as a result of the flattening and increased chord length $CL_1$ of the convex arch region 140 under the midstance arch force $F_{MSA}$ (i.e., compression of the arched shank 40 between the wearer's foot and the ground), the rear portion 56 of the arched shank 40 is displaced rearward and downward. Accordingly, the front portion 54 of the heel cup 30 is also displaced rearward and downward. Further, the downward displacement of the front portion 54 of the heel cup 30 causes the rear portion 52 of the heel cup 30 to be displaced upward. The upward displacement of the rear portion 52 of the heel cup 30 causes the heel cup 30 to rotate upwards and towards the heel region 4 of the foot 2. That is, the downward and rearward movement of the front portion 54 of the heel cup 30 due to the increased chord length $CL_1$ of the convex arch shank 40 in response to the midstance arch force $F_{MSA}$ causes upward movement of the rear portion 52 of the heel cup 30 which rotates the heel cup 30 towards the heel region 4 of the foot 2.

Accordingly, as the structure of the sole 16 is provided by the orthotic shell 10, the dynamic rotation of the heel cup 30 of the orthotic shell 10 in response to the midstance arch force $F_{MSA}$ causes the heel cup 130 of the sole 16 to rotate upwards and towards the heel region 4 of the foot 2. In some embodiments, the heel cup 30 may rotate substantially about the connection between the rear portion 56 of the arched shank 40 and the front portion 54 of the heel cup 30 such as the inflection point between the convex curvature of the arched shank 40 and the concave curvature of the heel cup 30. In some embodiments, the heel cup 30 and the arched shank 40 may be connected along their respective ends. As discussed herein, rotation of the heel cup 30 of the orthotic shell 10 causes rotation of the heel cup 130 of the flip-flop 12. Rotation of the heel cup 130 is indicated by the arrow R in FIG. 8.

With further reference to FIG. 8, the upward rotation of the heel cup 130 pushes the center base region 132 in contact with the heel 4 of the foot 2 and applies a midstance heel force $F_{MSH}$ upon the heel region 4 of the foot 2. The midstance heel force $F_{MSH}$ presses the heel cup 130 upward against the heel region 4 of the foot 2 such that the heel cup 130 actively engages the heel region 4 at midstance (footflat). The dynamic and active engagement of the heel region 4 increases the cradling and cupping effect of the heel cup 130 which further promotes proper alignment of the heel region 4 and healthy biomechanics of the wearer's foot and ankles. For example, the curved sidewall region 134 can cause the heel region 4 to align into the heel cup 130 along at least along the sagittal plane in midstance. Accordingly, the orthotic shell 10 can control foot 2 contact points and pressure along the sagittal plane in midstance via the heel cup 30 (and midfoot and forefoot portions 24, 26) as discussed herein. Further, the orthotic shell 10 via alignment and pressure of the heel cup 130 in midstance as discussed herein can control (e.g., substantially prevent or inhibit) roll of the foot 2 in the transverse plane relative to the orthotic/sandal.

Orthotic Support at Terminal Stance

Figure 9:
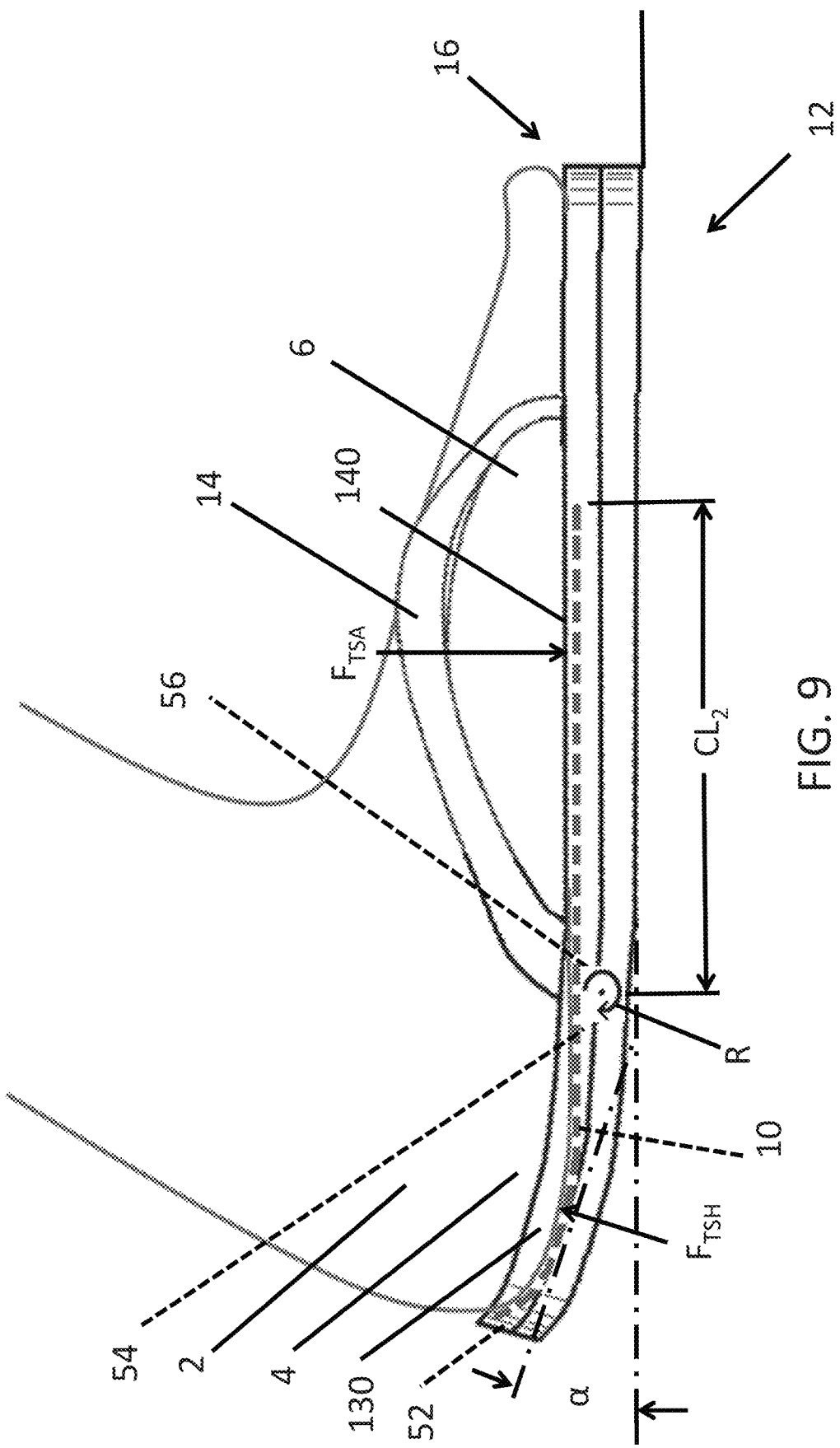
FIG. 9 illustrates the footwear in the sagittal plane fitted with an embodiment of the orthotic shell to illustrate the orthotic support provided by the sole at the terminal stance (heel-off) phase of the wearer's gait.

FIG. 9 illustrates the flip-flop 12 fitted with the orthotic shell 10 that is donned on a wearer's foot 2 at the terminal stance (heel-off) phase of gate. At terminal stance (heel-off), the weight of the wearer is gradually shifted forward from the heel region 4 to the midfoot region 6 as the heel region 4 of the foot 2 is lifted off the heel portion 122 of the sole 16. That is, at terminal stance (heel-off), weight is increasingly shifted over the arch region 140 of the sole 16 and less weight is positioned over the heel cup 130 until the heel region 4 of the foot 2 is lifted entirely or substantially entirely away (i.e., heel-off) from the base region 132 of the heel cup 130 and the heel region 4 is not in contact with the sole 16.

Accordingly, the magnitude of the terminal stance arch force $F_{TSA}$ applied by the midfoot region 6 of the foot 2 to the arch region 140 of the sole 16 at terminal stance (heel-off) may be greater than the magnitude of the midstance arch force $F_{MSA}$ at midstance (flat-foot). The increase in magnitude between the terminal stance arch force $F_{TSA}$ and the midstance arch force $F_{MSA}$ causes further flattening of the convex arch of the semi-rigid arched shank 40 and the arch region 140.

Whether or not the magnitude of the terminal stance arch force $F_{TSA}$ increases, the heel lifting relative to the support surface in the terminal stance provides travel clearance, space, or room, including room for rotational movement, to allow at least a portion of the base region 132 of the heel cup 130 (and corresponding portions of the footwear 12) to rise or translate generally upwards relative to the support surface due to the terminal stance arch force $F_{TSA}$ as illustrated in FIG. 9 relative to FIG. 8. Thus, in some embodiments, the heel lifting relative to the support surface in the terminal stance provides room for rotational movement to allow at least a portion of the base region 132 of the heel cup 130 (and corresponding portions of the footwear 12) to rise or translate generally upwards relative to the support surface due to the terminal stance arch force $F_{TSA}$ without an increase in the magnitude of the terminal stance arch force $F_{TSA}$. In some embodiments, the heel lifting relative to the support surface in the terminal stance provides room for rotational movement to allow at least a portion of the base region 132 of the heel cup 130 (and corresponding portions of the footwear 12) to rise or translate generally upwards relative to the support surface due to the terminal stance arch force $F_{TSA}$ with an increase in the magnitude of the terminal stance arch force $F_{TSA}$.

Further flattening of the arch region (longitudinally but not transversely) 140 at terminal stance (heel-off) causes the chord length of the convex curvature of the arch region 140 in the longitudinal direction to further increase from the chord length $CL_1$ at the midstance loaded state (shown in FIG. 8) to $CL_2$ at the terminal stance loaded state (shown in FIG. 9). Therefore, as a result of the increased chord length $CL_2$ of the further flattened arched shank 40, the front portion 54 of the heel cup 30 is pushed or displaced further rearward and downward which further rotates the heel cup 30 upwards and towards the heel region 4 of the foot 2 while maintaining transverse convex arch support lateral to medial. Rotation of the heel cup 130 is indicated by the arrow R in FIG. 9. In some configurations, the difference in length between $CL_2$ and $CL_1$ may be between 5 mm to 10 mm, including the foregoing values and ranges bordering therein. In other embodiments, the difference in length between $CL_1$ and $CL_0$ may be less than 5 mm or greater than 10 mm, including the foregoing values and ranges bordering therein.

The further upward rotation of the heel cup 130 causes the center base region 132 to apply a terminal stance heel force $F_{TSH}$ upon the heel region 4 of the foot 2. The midstance heel force $F_{TSH}$ actively presses the heel cup 130 upward and against the rising heel region 4 of the foot 2 such that the heel cup 130 actively engages the heel region 4 even as the heel region 4 is lifting upward between midstance and terminal stance. This dynamic and reactive rotation/movement of the heel cup 30 of the orthotic shell 10 causes the heel cup 130 of the sole 16 to prolong the contact with and support of the rising heel region 4 of the foot 2 (i.e., relative to a flat-soled flip-flop not fitted with the orthotic shell 10) until the heel region 4 rises beyond the reach of the heel cup 130. The extended engagement of the heel region 4 of the foot 2 as the heel region 4 is rising or lifting off from the sole 16 increases the amount of time that the heel region 4 is supported by the sole 16 during gait movement. That is, the rising heel cup 130 decreases the amount of time that the heel region 4 is unsupported between the terminal stance (heel-off) and initial contact (heel-strike) phase of gait. In other words, the heel region 4 is cradled and cupped by the heel cup 130 as the sole 16 dynamically rotates toward the heel region 4 such that the heel cup 130 actively engages the heel region 4 even as the heel region 4 is lifting upward.

Figure 11:
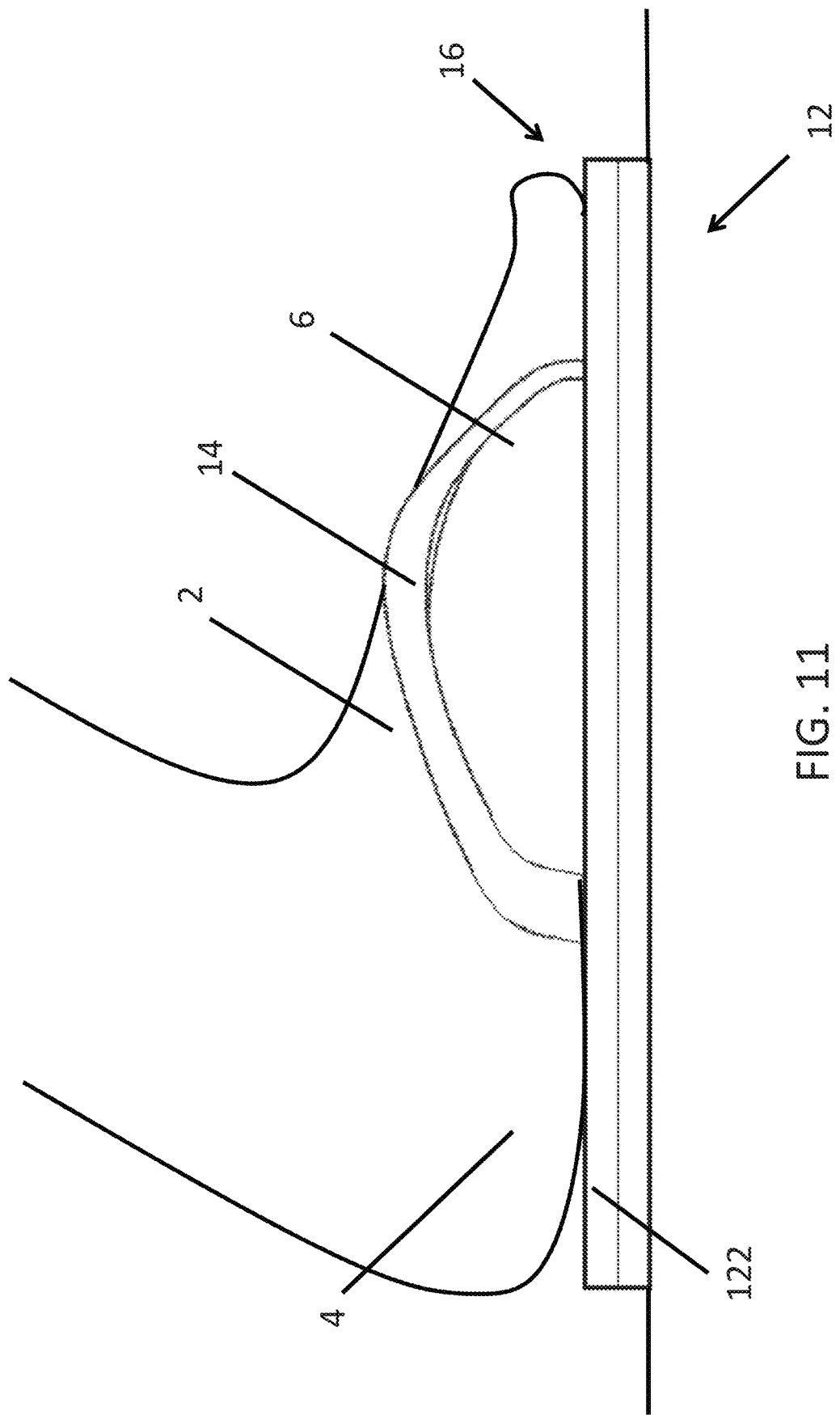
FIG. 11 illustrates the footwear in the sagittal plane without the orthotic shell installed at the terminal stance (heel-off) phase of the wearer's gait.

For comparison, FIG. 11 illustrates a flat-soled flip-flop 12 donned on the foot 2 at the terminal stance (heel-off) phase of gate. As shown, the heel region 4 has lifted away from the heel portion 122 of the sole 16 and the heel region 4 is entirely or substantially entirely unsupported in the transverse plane 154, the frontal plane 156, and the sagittal plane 158 by the sole 16 at least in the terminal stance. As a result, the sole 16 dangles from the foot 2 between terminal stance (heel-off) and initial contact (heel-strike) phases which causes compensatory foot adjustment such as toe flexion/extension and/or foot adduction/abduction. For example, the curved sidewall region 134 can cause the heel region 4 to align into the heel cup 130 along at least along the sagittal plane in terminal stance. Accordingly, the orthotic shell 10 can control foot 2 contact points and pressure along the sagittal plane in terminal stance via the heel cup 30 (and midfoot and forefoot portions 24, 26) as discussed herein. Further, the orthotic shell 10 via alignment and pressure of the heel cup 130 in terminal stance as discussed herein can control (e.g., substantially prevent or inhibit) roll of the foot 2 in the transverse plane relative to the orthotic/sandal.

Figure 15:
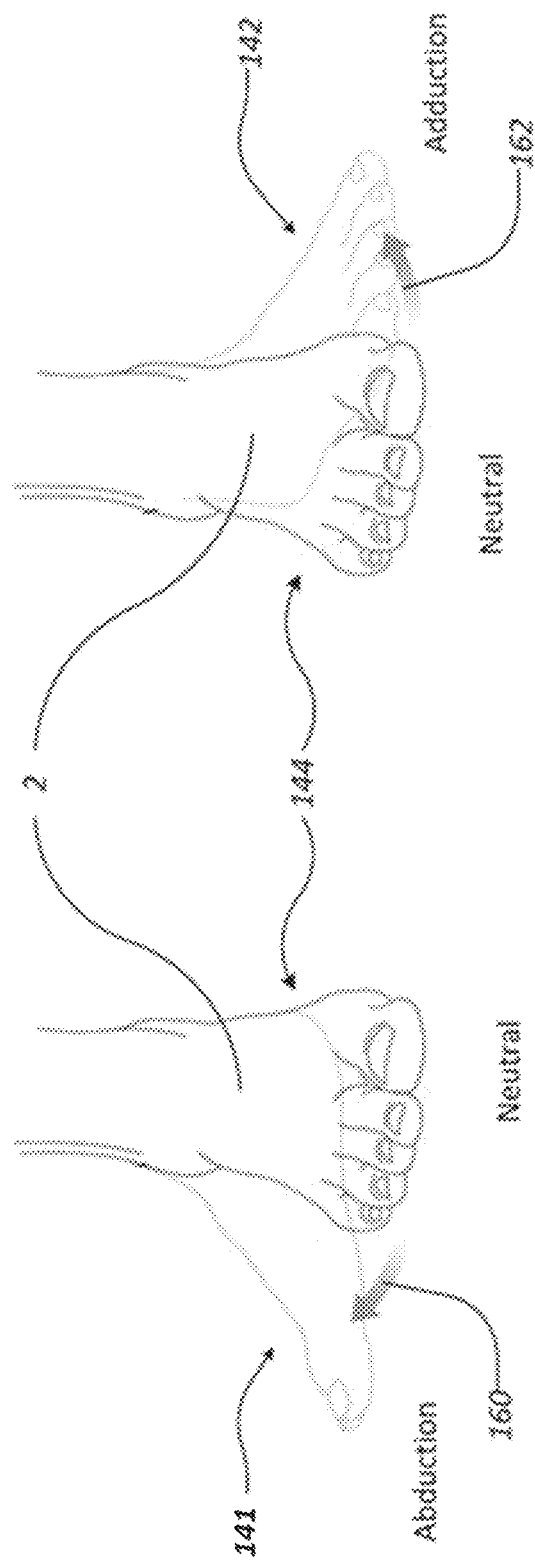
FIG. 15 illustrates abduction and adduction of the foot versus a neutral position.

For reference, as illustrated in FIG. 15, abduction 141 can refer to motion that moves the foot 2 (e.g., the forefoot such as the foot area with the toes) away from a center or vertical centerline of a body along the transverse plane 154 as illustrated by abduction direction 160. Stated differently, abduction 141 can refer to a motion that pulls the foot 2 (e.g., the forefoot) away from the midline of the body along the transverse plane 154 as illustrated by abduction direction 160. Adduction 142 can refer to motion that moves the foot 2 (e.g., the forefoot such as the foot area with the toes) toward a center or vertical centerline of a body along the transverse plane 154 as illustrated by adduction direction 162. Stated differently, adduction 142 can refer to a motion that pulls the foot 2 (e.g., the forefoot) toward the midline of the body along the transverse plane 154 as illustrated by adduction direction 162.

In contrast, the flip-flop 12 fitted with the orthotic shell 10 of the present disclosure, provides a dynamic and reactively rotating sole 16 which positions the heel cup 130 closer to the foot 2, which prolongs the engagement between the wearer's heel region 4 and the heel cup 130 of the sole 16. This allows for a more natural gait particularly in a flip-flop due to prolonged contact between the foot 2 and the sole 16. Accordingly, there is less need for compensatory foot adjustment such as toe flexion/extension and/or foot adduction/abduction. Further, the prolonged contact may decrease the effects of prolonged flip-flop use such as, but not limited to, shortening of the stride, ankle dorsiflexion and toe fatigue due to curling of the toes in order to grasp the center post of the Y-shaped strap of the flip-flop. In other words, the muscles in the foot 2 may work less to retain the flip-flop 12 on the foot 2, which may improve comfort and biomechanics of the foot relative to flat-soled flip-flops.

Accordingly, an increase in time of and extending heel region 4 support (by the heel cup 130 as discussed herein) into the terminal stance (e.g., increasing duration of contact ad support into terminal stance), minimizes the time (e.g., at least through part of the terminal stance) which a person, for example, curls their toes or otherwise exerts effort to retain the flip-flop 12 on the foot 2 in a desired position. The assistance, even just for between 1 to 100 milliseconds, to hold the heel cup 130 to the heel region 4 via the orthotic shell 10 can help lessen toe strain, reduce foot fatigue, and improve gait. Further, the assistance to hold the heel cup 130 to the heel region 4 via the orthotic shell 10 can help prep for heel strike landing by having the flip-flop 12 in a better or more desired position (e.g., predetermined position even though the orthotic shell 10 may no longer be actively assisting at heel strike.

The prolonged contact between the heel region 4 of the foot 2 and the heel cup 130 also prolongs the alignment between the foot 2 and the sole 16. Accordingly, the heel cup 130 is more closely aligned and centered with the heel region 4 upon each heel strike. That is, the prolonged contact shortens the amount of time that the foot 2 and the sole 16 are separated between terminal stance (heel-off) and initial contact (heel-strike) phases. This may ensure that the heel cup 130 is more closely centered with the heel region 4 upon each heel-strike when compared to a flat-soled flip-flop.

Figure 10:
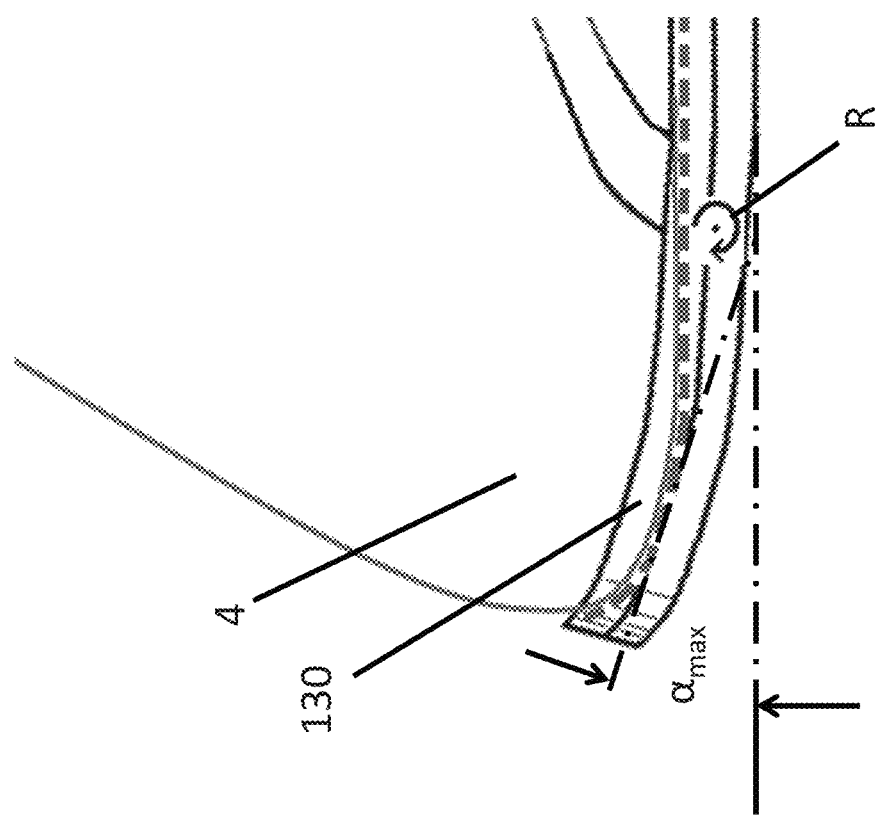
FIG. 10 is a close-up view of the heel portion of the footwear in the sagittal plane fitted with an embodiment of the orthotic shell to illustrate the maximum angle of rotation by the heel cup of the sole.

As described above, the heel cup 130 rotates and presses against the heel region 4 of the foot 2, which applies the terminal stance heel force $F_{TSH}$ upon the heel region 4 of the foot 2. As shown in FIG. 9, the terminal stance heel force $F_{TSH}$ is applied at an angle α relative to the midstance heel force $F_{MSH}$. For comparison, the midstance heel force $F_{MSH}$ in FIG. 8 is applied to the heel region 4 by the heel cup 130 in a substantially vertical direction. The heel cup 130 applies the terminal stance heel force $F_{TSH}$ at the angle α due to the dynamic rotation of the heel cup 130 from the midstance (foot-flat) to terminal stance (heel-off) phases of gait. The angle α increases as the heel cup 130 rotates due to the increase of the terminal stance arch force $F_{TSA}$ and the heel region 4 lifting away from and off the sole 16. The angle α increases to a maximum angle $α_{max}$ at the position where the heel region 4 is no longer in contact with the heel cup 130, as shown in FIG. 10. In other words, the magnitude of the terminal stance heel force $F_{TSH}$ equals zero. Accordingly, the maximum angle $α_{max}$ defines the maximum range of rotation by the heel cup 130. In some embodiments, the maximum angle $α_{max}$ may be a value between 15 degrees to 30 degrees, including the foregoing values and ranges bordering therein. In other embodiments, the maximum angle $α_{max}$ may be less than 15 degrees or greater than 30 degrees.

The semi-rigid construction of the orthotic shell 10 allows the chord length of the arch region 140 to vary in length such that the heel cup 130 rocks and rotates dynamically during the loading response phase of the wearer's gait. Orthotic insoles formed from non-rigid materials such as foam will merely compress downward under the weight of the wearer. That is, arch region of a foam orthotics would not increase in chord length and facilitate rotation of the heel cup. Orthotic insoles formed from rigid materials lack the flexibility to allow flattening of the arch region and an increase in chord length to facilitate rotation of the heel cup. They are static in stance and not functional.

In some embodiments, the shape of the orthotic shell 10 may vary to provide various levels of support to enhance the comfort and/or compensate for accommodate a variety of foot abnormalities or deformities. For example, in some embodiments, the forefoot portion 26 may have metatarsal pads formed thereon to improve the comfort of the orthotic shell 10 within the forefoot portion 26.

In some embodiments, the shape of each of the heel portion 22, the midfoot portion 24 and the forefoot portion 26 may vary to accommodate the shape of a wearer's foot. Similarly, the position of each of the heel, midfoot and forefoot portions 22, 24, 26 relative to each other may vary to accommodate the shape of a wearer's foot.

In some embodiments, the orthotic shell 10 may have varying thicknesses between the heel, midfoot and forefoot portions 22, 24, 26. In some configurations, the thicknesses may be varied according to the desired bending strength, torsional rigidity, stiffness, deflection amount, etc. of the orthotic shell 10. For example, the thickness in a region of the orthotic shell 10 may be thicker to reduce flexibility of the orthotic shell 10 within that region. Similarly, the thickness across the heel, midfoot and forefoot portions 22, 24, 26 may be varied such that the orthotic shell 10 may accommodate varus and valgus foot deformities and/or flexible and rigid foot deformities. Similarly, the heel, midfoot and forefoot portions 22, 24, 26 may be formed from differing materials or constructions such that the rigidity, stiffness and/or flexibility of each portion is optimized. In some embodiments, the heel, midfoot and forefoot portions 22, 24, 26 may comprise structural enhancers such as, but not limited to, ribs, pleats, fillets, recesses, etc. to provide rigidity or flexibility in the desired portion.

Figure 17:
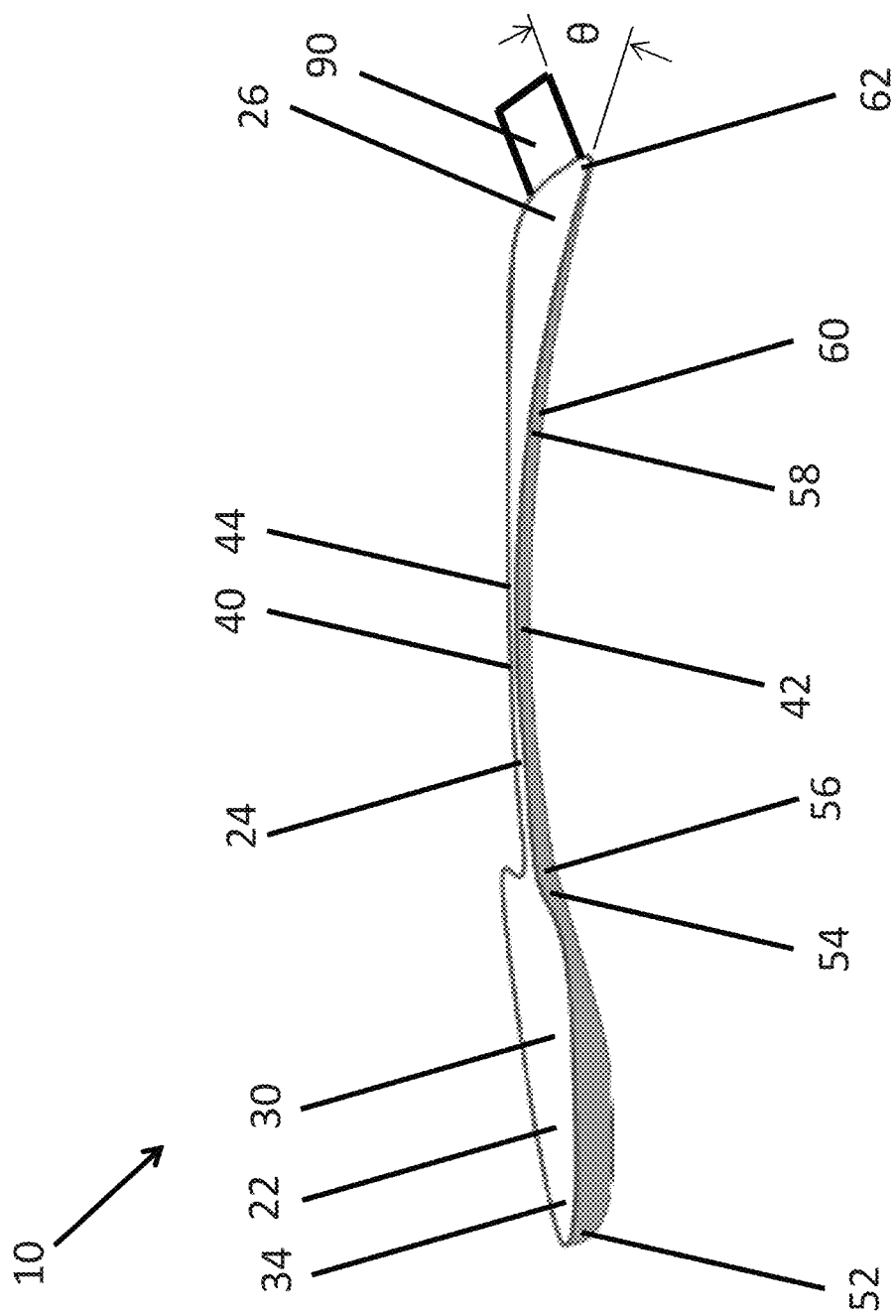
FIG. 17 illustrates an alternative embodiment of the orthotic shell viewed in the sagittal plane, the orthotic shell provided with a distal extension portion.
Figure 18A:
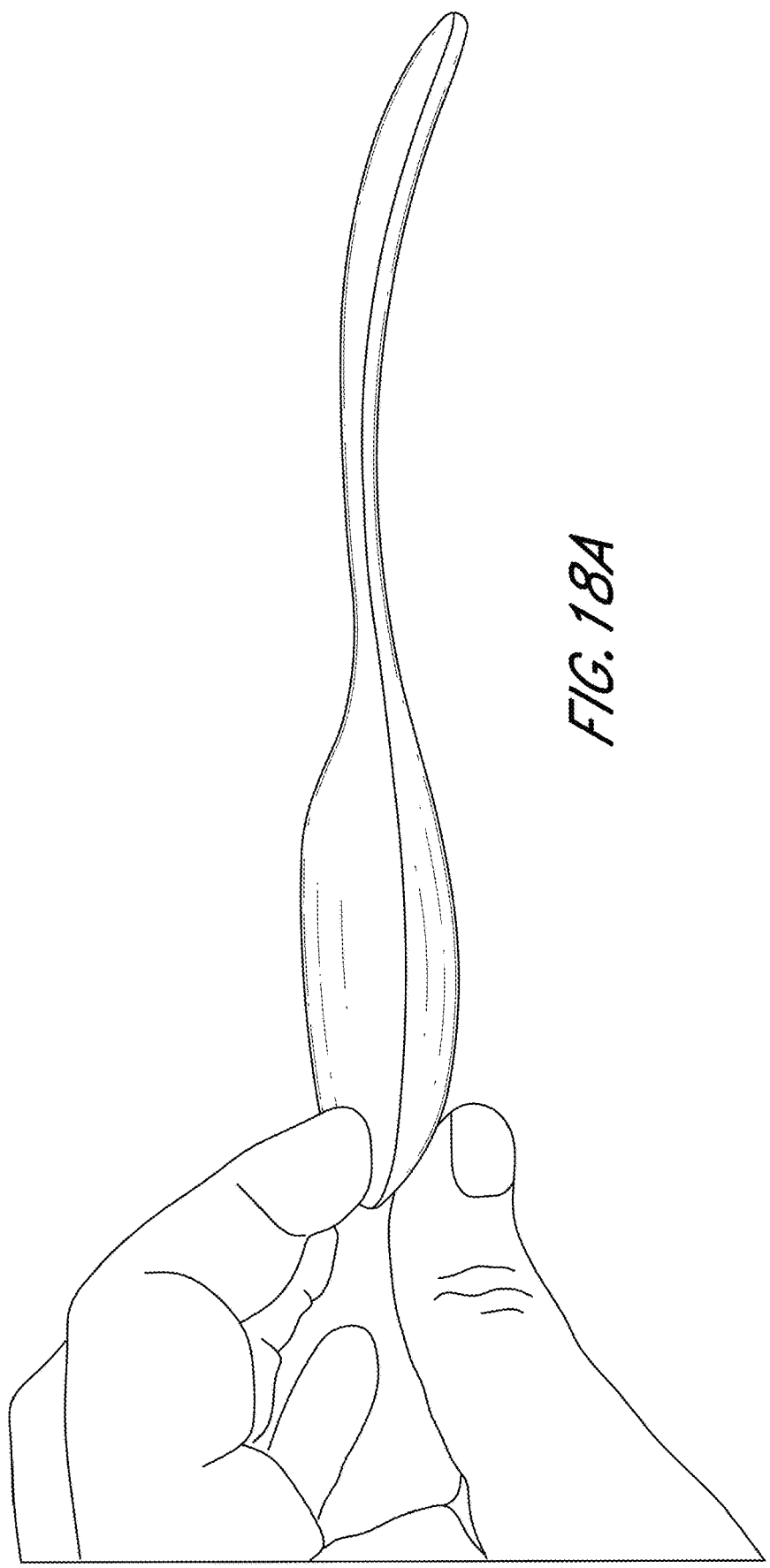
FIGS. 18A-18H show images of an embodiment of a Soloha orthotic.
Figure 18B:
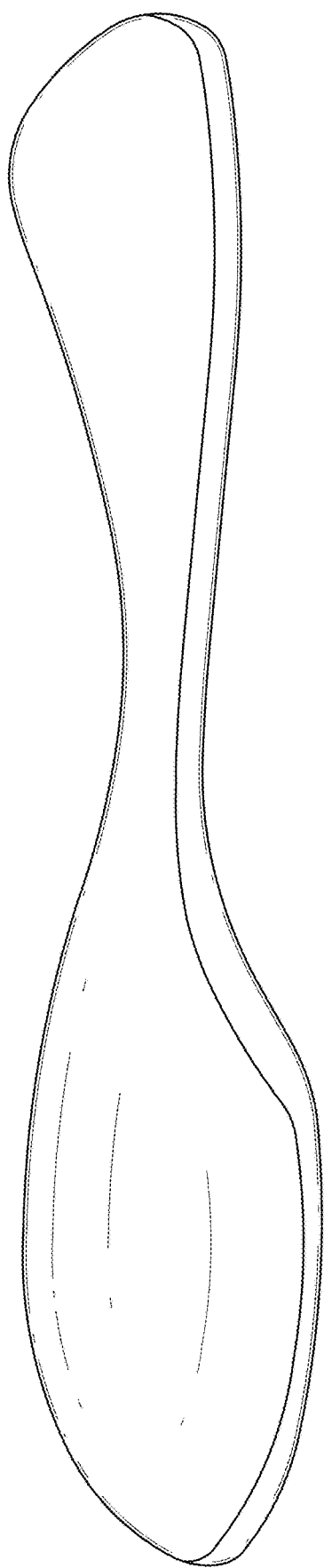
Figure 18C:
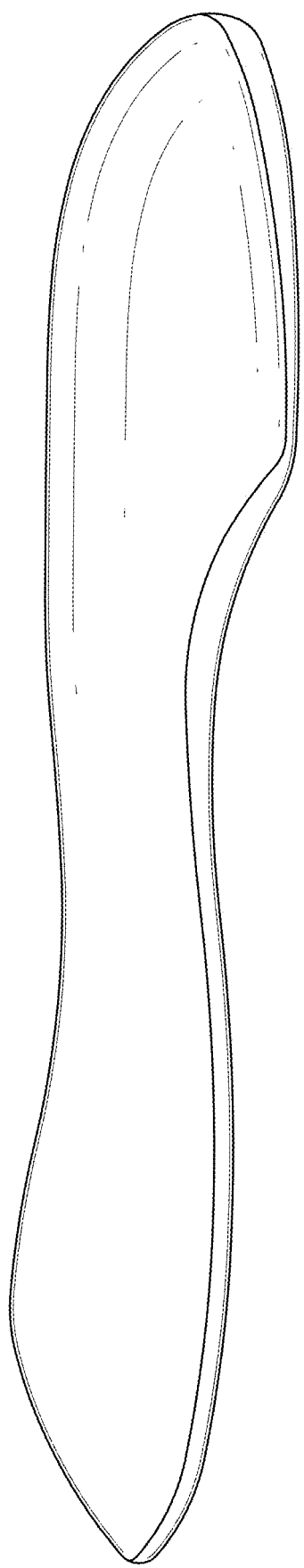
Figure 18D:
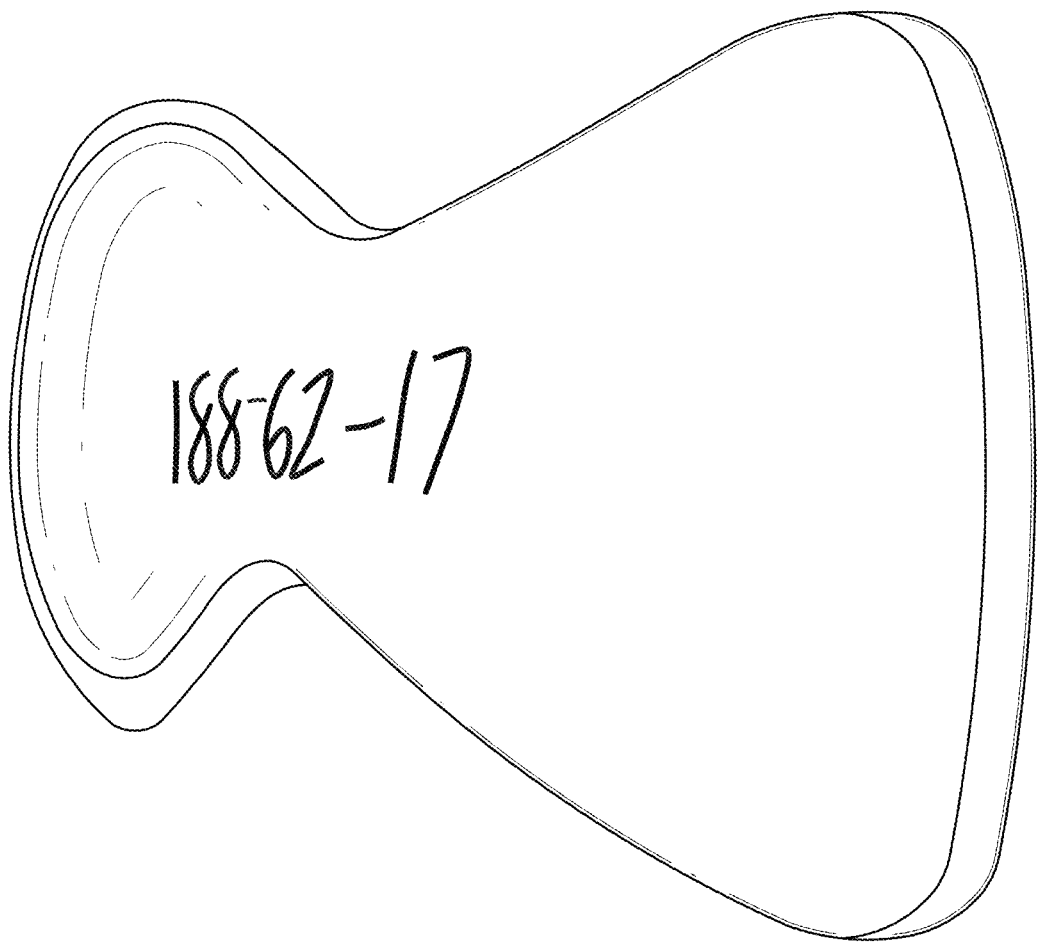
Figure 18E:
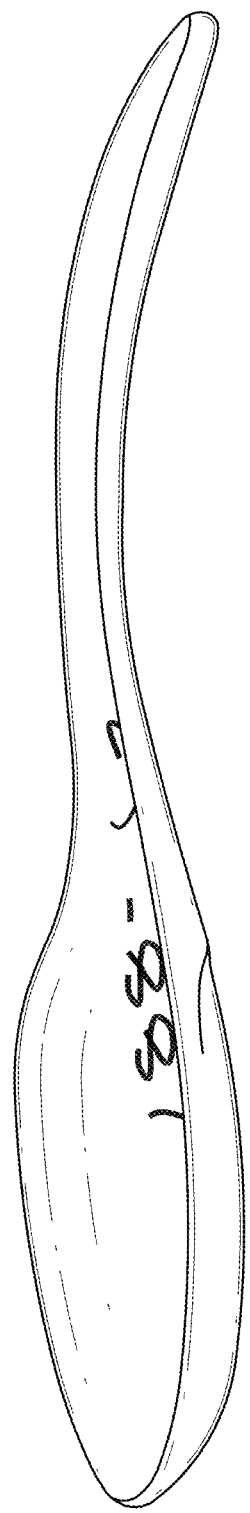
Figure 18F:
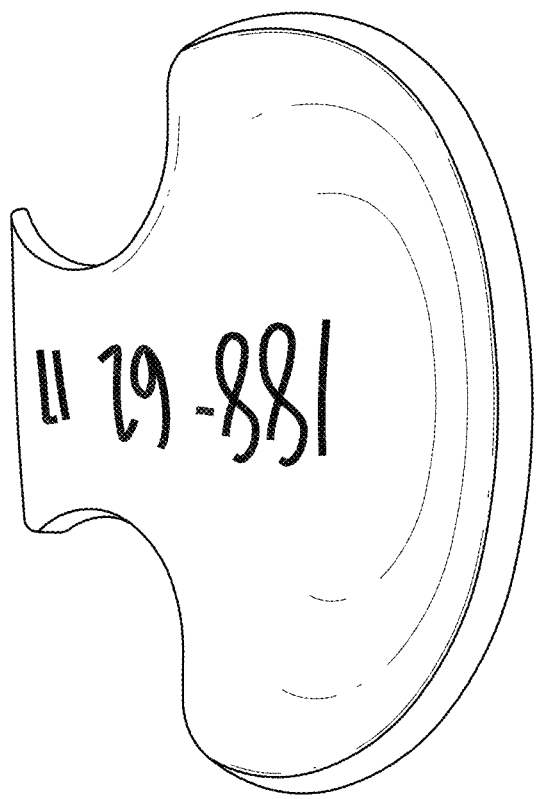
Figure 18G:
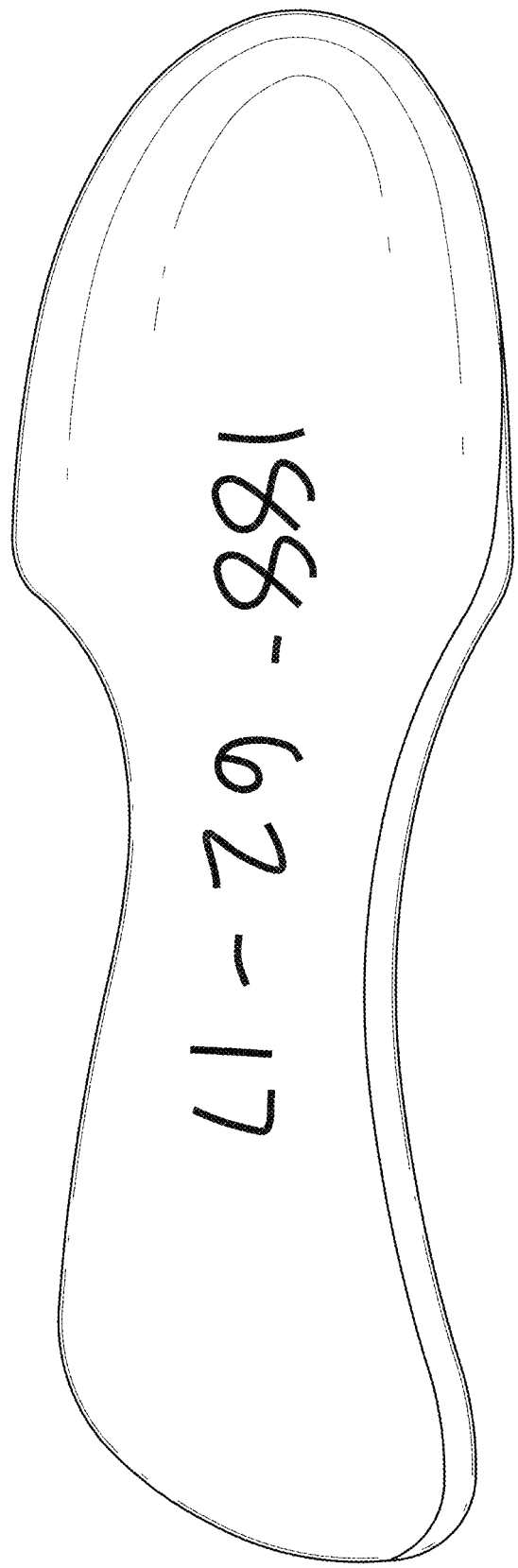
Figure 18H:
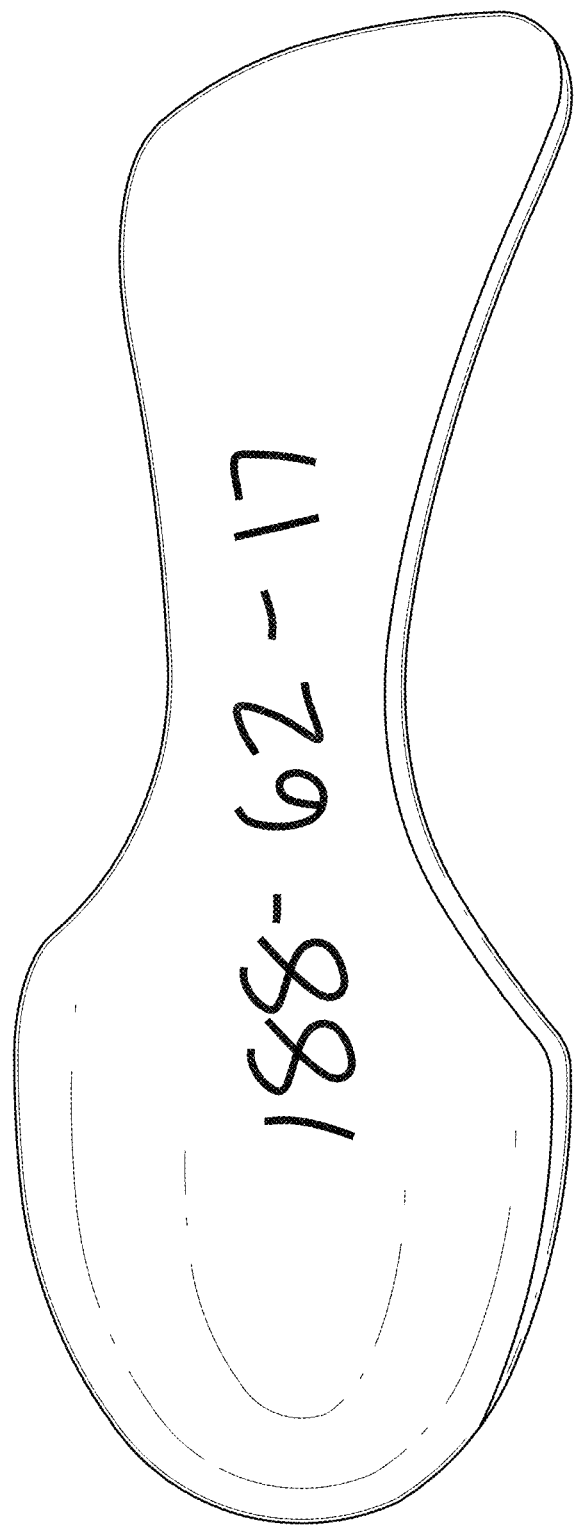

In some embodiments, the orthotic shell 10 may be provided with a distal extension, angled extension, or distal angled lever 90 positioned forward of the front portion 62 of the forefoot portion 26 when viewed in the sagittal plane, as shown in FIG. 17. The distal extension portion 90 may be angled relative to the forefoot portion 26 and extends away from the front portion 62 of the forefoot portion 26. The distal extension portion 90 extends a distance in a direction towards the metatarsal heads and sulcus of the foot from the forefoot portion 26 such that the distal extension portion 90 supports the metatarsal heads and sulcus of the foot. That is, the distal extension portion 90 has a length and a width such that the distal extension portion 90 engages the metatarsal heads and sulcus of the foot.

In some configurations, the distal extension portion 90 may have a width that is similar or matches the width of the forefoot portion 26. In other configurations, the distal extension portion 90 may have a width that is narrower or wider than the width of the forefoot portion 26. In some configurations, the distal extension portion 90 may have a thickness that is similar or matches the thickness of the forefoot portion 26. In other configurations, the distal extension portion 90 may have a thickness that is thinner or thicker than the thickness of the forefoot portion 26.

The distal extension portion 90 extends from the front portion 62 of the forefoot portion 26 so as to form a lever or rocker arm. In use, the downward force of the foot sulcus and plantar metatarsal heads on the distal extension portion 90 provide a lever effect and/or a rocking-effect on the orthotic shell 10. That is, the downward force on the distal extension portion 90 causes the heel cup 30 to move upwards as the orthotic shell 10. The upward movement of the heel cup 30 is caused by rocking or rotation about the front portion 62 of the forefoot portion 26 such that the heel cup 130 and the arch region 140 of the sole 16 is rotated towards the foot 2. That is, in addition to the dynamic rotation of the heel cup 30 provided by the heel cup 130 of the sole 16 at terminal stance, the downward force of the foot sulcus and plantar metatarsal heads on the distal extension portion 90 causes further dynamic rotation of the sole 16 which increases contact of the sole 16 with the foot 2 beyond midstance and into the toe-off phase of gait.

The rotation of the orthotic shell 10 caused by the distal extension portion 90 prolongs the contact between the wearer's foot 2 and the heel cup 130 and the midfoot arch region 140 of the sole 16 of the flip-flop 12 beyond midstance and into the toe-off phase of gait. That is, this contact further prolongs the contact into heel off and early swing phases of gait due to the foot sulcus and plantar metatarsal heads pressing down on the distal extension portion 90. The closer and more prolonged interface allows for a more natural gait due to better and prolonged contact and less need for compensatory foot/gait adjustment such as shortened stride, increased cadence and toe flexion/extension and or foot adduction/abduction.

In some embodiments, the distal extension portion 90 may extend towards the foot of the wearer at an angle $\theta$ relative to the forefoot portion 26 or a portion of the forefoot portion 26 near the end of the forefoot portion 26. As illustrated in FIG. 17, the distal extension portion 90 may be angled upward to extend at least in part toward insole portion 18 or away from outsole portion 20 (and toward a front of the sole 16). In some embodiments, the angle $\theta$ of the distal extension portion 90 may be a value between 15 degrees to 30 degrees, including the foregoing values and ranges bordering therein. In other embodiments, the angle $\theta$ may be less than 15 degrees or greater than 30 degrees.

In some embodiments, the distal extension portion 90 may have a thickness similar to the heel, midfoot and forefoot portions 22, 24, 26. In other embodiments, the distal extension portion 90 may vary in thickness relative to the heel, midfoot and forefoot portions 22, 24, 26 according to the desired bending strength, torsional rigidity, stiffness, deflection amount, etc. of the orthotic shell 10 as discussed herein. For example, the thicker or relatively thicker the heel, midfoot and/or forefoot portions 22, 24, 26, the greater the thickness of the distal extension portion 90. Or the thinner or relatively thinner the heel, midfoot and/or forefoot portions 22, 24, 26, the thinner the thickness of the distal extension portion 90. Or the thinner or relatively thinner the heel, midfoot and/or forefoot portions 22, 24, 26, the thicker the thickness of the distal extension portion 90. Or the thicker or relatively thinner the heel, midfoot and/or forefoot portions 22, 24, 26, the thinner the thickness of the distal extension portion 90. In some embodiments, the distal extension portion 90 may vary in thickness along its length and width to provide the desired bending strength, torsional rigidity, stiffness, deflection amount, etc. of the distal extension portion 90.

In some embodiments, a portion of the distal extension portion 90 may have a curved shape so as to facilitate and/or encourage the rocking motion of the orthotic shell 10. For example, an underside of the distal extension portion 90 (i.e., a portion of the distal extension portion 90 facing the outsole portion 20) may be curved such that the orthotic shell 10 is able to roll along the curvature when the downward force on the distal extension portion 90 is applied by the foot sulcus and plantar metatarsal heads. The rolling along the curvature may provide a gradual rocking motion which further prolongs the contact into heel off and early swing phases of gait. In other embodiments, an entirety of the distal extension portion 90 may have a curved shape. In some embodiments, the shape and geometry of the curvature may vary along the length, width and thickness directions of the distal extension portion 90 and/or the orthotic shell 10 to provide the desired amount, range and rate of rocking motion.

In some embodiments, the sole 16 can be molded around the orthotic shell 10 as opposed to being sandwiched between the insole and outsole portions 18, 20 of the sole 16. For example, in some embodiments, during the injection molding process of the sole 16, the orthotic shell 10 may be inserted into the mold cavity such that the sole 16 is formed onto and/or around the orthotic shell 10. Similarly, in other embodiments, either one of the insole and outsole portions 18, 20 can be first molded around the orthotic shell 10 and bonded to the other of the insole and outsole portions 18, 20. For example, the insole portion may be formed onto the orthotic shell 10 such that the orthotic shell 10 comprises at least a portion of the outsole portion 20. As another example, the orthotic shell 10 may be part of or form the insole portion 18 and may have direct or at least partial direct contact with the foot 2. Accordingly, the orthotic shell 10 would not be enclosed and may be externally visible when the sole is fully assembled.

In some embodiments, the orthotic shell 10 may be shaped such that the heel portion 24 is rotated relative to the midfoot portion 24 and the forefoot portion 26. FIGS. 12A, 12B, and 12C illustrate the orthotic shell 10 with respect to the transverse plane 154. As shown, the heel cup 30 is rotated relative to the midfoot portion 24 and the forefoot portion 26 such that a longitudinal centerline 80 of the heel cup 30 forms an angle β relative to the longitudinal centerline 82 of the heel cup 30. FIG. 12A illustrates the heel cup rotate towards the lateral side 44 of the orthotic shell 10. FIG. 12B illustrates the heel cup rotate towards the medial side 42 of the orthotic shell 10. In some embodiments, the angle β may be a value between 5 degrees to 15 degrees, including the foregoing values and ranges bordering therein. In other embodiments, the maximum angle β may be less than 5 degrees or greater than 15 degrees. The rotated heel cup 30 or the orthotic shell 10 may accommodate wearers having adduction/abduction of the midfoot and forefoot. FIG. 12C illustrates an embodiment of the orthotic shell with respect to the transverse plane with the heel cup rotated either toward the medial side or toward the lateral side of the orthotic shell.

FIGS. 12A, 12B, and 12C illustrate the orthotic shell 10 with respect to the transverse plane 154. In some embodiments, the orthotic shell 10 may be shaped such that the heel portion 24 is rotated or protruded (bulged) relative to the midfoot portion 24 and the forefoot portion 26. In some embodiments, the orthotic shell 10 may be shaped such that the heel portion 24 is rotated or protruded (bulged) about 1 mm to 10 mm relative to the midfoot portion 24 and the forefoot portion 26. In some embodiments, the orthotic shell 10 may be shaped such that the heel portion 24 is rotated or protruded (bulged) about 0.5, 1, 2.5, 5, 7.5, 10, 12.5, 15, 17.5, or 20 mm, or a value within a range defined by any two of the aforementioned values relative to the midfoot portion 24 and the forefoot portion 26.

In some embodiments, each of the heel portion 24, the midfoot portion 24 and the forefoot portion 26 may be rotated relative to each other towards the medial side 42 or the lateral side 44 of the orthotic shell 10. Similarly, each of the heel portion 24, the midfoot portion 24 and the forefoot portion 26 may be rotated relative to each other in the transverse plane 154, the frontal plane 156, and the sagittal plane 158. Accordingly, the orthotic shell 10 may have a shape that provides orthotic support to a variety of shapes of wearers' feet.

Soloha Orthotic

In some embodiments, the orthotic is a Soloha orthotic (FIGS. 18A-18H, and Example 1). In some embodiments, the orthotic can be customized to a person's foot, for example, impression casted, scanned, photographed, 3D printed, and the like. In some embodiments, the orthotic can be used as a removable shoe orthotic. In some embodiments, the orthotic can be used as a transferable shoe orthotic. In some embodiments, the Soloha orthotic can be used as a removable and transferable shoe orthotic.

A embodiment of the Soloha orthotic is shown in FIGS. 18A-18H. In some embodiments, the orthotic (e.g., a Soloha orthotic) allows for deflection to occur with midfoot loading of the transverse arch of the foot. In other words, the arched shank of the Soloha orthotic is configured such that when a downward force is applied on the arched shank the arched shank deflects in such a way that the heel cup of the orthotic is reactively rotated toward the heel region of the foot. As shown in FIG. 9, the heel cup 130 rotates and presses against the heel region 4 of the foot 2, which applies the terminal stance heel force $F_{TSH}$ upon the heel region 4 of the foot 2. The terminal stance heel force $F_{TSH}$ is applied at an angle α relative to the midstance heel force $F_{MSH}$. For comparison, the midstance heel force $F_{MSH}$ in FIG. 8 is applied to the heel region 4 by the heel cup 130 in a substantially vertical direction. The heel cup 130 applies the terminal stance heel force $F_{TSH}$ at the angle α due to the dynamic rotation of the heel cup 130 from the midstance (foot-flat) to terminal stance (heel-off) phases of gait. The angle α increases as the heel cup 130 rotates due to the increase of the terminal stance arch force $F_{TSA}$ and the heel region 4 lifting away from and off the sole 16. The angle α increases to a maximum angle $α_{max}$ at the position where the heel region 4 is no longer in contact with the heel cup 130, as shown in FIG. 10. In other words, the magnitude of the terminal stance heel force $F_{TSH}$ equals zero. Accordingly, the maximum angle $α_{max}$ defines the maximum range of rotation by the heel cup 130. In some embodiments, the maximum angle $α_{max}$ may be a value between 15 degrees to 30 degrees, including the foregoing values and ranges bordering therein. In other embodiments, the maximum angle $α_{max}$ may be less than 15 degrees or greater than 30 degrees. In some embodiments, the maximum angle $α_{max}$ may range between 10 degrees to 35 degrees. In some embodiments, the maximum angle $α_{max}$ is about 5, 10, 15, 20, 25, 30, 35, or 40 degrees, or a value within a range defined by any two of the aforementioned values.

EXAMPLE(S)

The following example(s) is non-limiting.

Example 1

Gait Exam Comparison Between Standard Flip-Flop Sandal and Soloha Orthotic Sandal Potential adverse gait changes caused by wearing flip-flops compared to wearing normal shoe gear on manmade surfaces is typically noted using four (4) parameters: Stride Length (SL), Ankle Attack Angle (AAA), Stance Time (ST) and Frontal Plane Control of the Heel (FPCH). In this study, also included were abnormalities of Extensor and Flexor Substitution as well as Abductor Twist which appear in most flip flop gait examinations—these are typically seen in abnormal barefoot gait evaluations and are exaggerated in flip-flops due to compensations.

Standard flip flops cause a comparative shortened Stride Length, Larger Ankle Attack Length, Shorter Stance Time and minimal to no Frontal Plane Heel Control as well as Extensor/Flexor Substitution and Abductor Twist.

Four persons of normal BMI and without any history of lower extremity pathology were gait examined with standard flip-flops compared to Soloha orthotic sandals on both feet. One male and one female with forefoot valgus reducible cavo-varus foot types and one male and one female with forefoot varus reducible plano-valgus foot types.

All four patients in gait analysis exhibited a visual improvement when wearing the Soloha sandals compared to the standard flip-flop in three (3) of the four (4) standard parameters; SL, ST and FPCH as well as reduction of Flexor Substitution in swing phase and near elimination Abductor Twist. AAA was difficult to assess visually but appeared to be slightly increased in the cavus foot types and less in the planus foot types. Heel strike contact was invariably centered in the Soloha where in the standard flip-flop heel strike was consistently medially off center.

The Soloha sandal provided a more normal "shod foot gait" when compared to standard flip-flops with visual gait exam that exhibited a longer Stride Length, longer Stance Time and significant Frontal Plane Heel Control in both foot types, male and female with reduced maximal heel eversion and inversion. The Soloha sandal gait appeared more stable and propulsive and with improved patellar tracking than that of the standard flip-flop gait.

All four participants indicated significant improved comfort and stability in the Soloha sandal compared to the standard flip-flop.

Although embodiments have been shown and described herein as a flip-flop sandal or components for a flip-flop sandal, it is appreciated that aspects and features of the embodiments may be applied to a wide range of footwear, including without limitation, athletic shoes, casual shoes, dress shoes, work boots and recreational footwear.

While certain embodiments have been described, these embodiments have been presented by way of example only, and are not intended to limit the scope of the disclosure. Indeed, the novel methods and systems described herein may be embodied in a variety of other forms; furthermore, various omissions, substitutions and changes in the form of the described methods and systems may be made without departing from the spirit of the disclosure. The accompanying claims and their equivalents are intended to cover such forms or modifications as would fall within the scope and spirit of the disclosure.

What is claimed is:

1. Orthotic footwear worn on a foot of a wearer, the footwear comprising an orthotic device, the footwear comprising:
    a flat non-contoured sole comprising a surface that is substantially planar, and
    an orthotic device comprising a layer of semi-rigid material, the orthotic device positioned in the flat non-contoured sole, the orthotic device comprising:
        a heel portion configured to support a heel region of the foot, and
        a midfoot portion connected to the heel portion and configured to support an arch region of the foot, the midfoot portion comprising an arched shank having a curved convex shape,
    wherein the arched shank is configured to deflect under a downward force applied thereon which increases a chord length of the arched shank in a longitudinal direction such that the layer of semi-rigid material corresponding to the curved convex shape of the arched shank becomes relatively flatter with the downward force causing the deflection of the arched shank, and
    wherein the increase in the chord length causes reactive rotation of the heel portion toward the heel region of the foot, causing the layer of semi-rigid material corresponding to the heel portion to rotate toward the heel region of the foot such that a part of the flat non-contoured sole rotates toward the heel region of the foot.

2. The orthotic footwear of claim 1, wherein the heel portion is configured to rotate toward and applies a force to the heel region of the foot at a midstance phase of gait.

3. The orthotic footwear of claim 1, wherein the heel portion is configured to rotate toward and applies a force to the heel region of the foot at a terminal stance phase of gait.

4. The orthotic footwear of claim 1, wherein the heel portion further comprises a concave heel cup, the heel cup comprising:
    a base region configured to support a bottom of the heel region; and
    a curved concave outer sidewall region extending radially outward and upward from the base region in a direction away from the base region the outer sidewall region configured to support an outer periphery of the heel region.

5. The orthotic footwear of claim 1, wherein the heel portion is configured to rotate between 15 degrees to 30 degrees at a heel-off phase of gait.

6. The orthotic footwear of claim 1, the orthotic device further comprising:
    a forefoot portion connected to the midfoot portion and configured to support metatarsal heads of the foot.

7. The orthotic footwear of claim 6, wherein the orthotic device further comprises a distal extension portion connected to the forefoot portion and configured to support sulcus and plantar metatarsals of the foot.

8. The orthotic footwear of claim 7, wherein the distal extension portion is angled relative to the forefoot portion.

9. The orthotic footwear of claim 1, wherein the midfoot portion and the forefoot portion are configured to support the central three metatarsals of the foot.

10. The orthotic footwear of claim 1, wherein the orthotic device is formed from plastic material.

11. The orthotic footwear of claim 1, wherein the orthotic device has a thickness greater than 3 mm.

12. The orthotic footwear of claim 1, wherein, in use, the orthotic device is enclosed within the sole.

13. The orthotic footwear of claim 1, wherein the orthotic device is more rigid than the sole.

14. The orthotic footwear of claim 1, the sole further comprising an insole portion and an outsole portion, wherein the orthotic device is positioned between the insole and outsole portions.

15. The orthotic footwear of claim 1, wherein the orthotic device has a longitudinal length that is between one-half to four-fifths of a longitudinal length of the sole.

16. The orthotic footwear of claim 1, wherein the orthotic device has a longitudinal length that is greater than four-fifths of a longitudinal length of the sole.

17. Orthotic footwear comprising:
a flat sole comprising an insole portion and an outsole portion,
an orthotic shell comprising a layer of semi-rigid material, the orthotic shell positioned between the insole portion and the outsole portion, the orthotic shell comprising:
a concave region that is configured to support a heel region of a foot; and
a convex region at an end of the concave region, the convex region being configured to support an arch region of the foot;
wherein the convex region is configured to deflect under a downward force applied thereon which increases a chord length of the convex region in a longitudinal direction such that the layer of semi-rigid material corresponding to the convex region becomes relatively flatter with the downward force causing the deflection of the convex region, and
wherein the increase in the chord length causes reactive rotation of the concave region toward the heel region of the foot causing the layer of semi-rigid material corresponding to the concave region to rotate toward the heel region of the foot such that a part of the flat sole rotates toward the heel region of the foot, and
wherein the orthotic shell is configured to provide dynamic orthotic support to a foot of a wearer; and
a strap configured to retain a top portion of the foot without restraining the heel region of the foot.

18. A method for manufacturing a sole that provides dynamic orthotic support to a foot of a wearer, the method comprising:
providing an orthotic shell according to claim 17 wherein the orthotic shell having a rigidity that is greater than the insole portion and the outsole portion;
positioning the orthotic shell between the insole portion and the outsole portion;
bonding the insole portion to the outsole portion such that the orthotic shell is enclosed within the sole; and
conforming a shape of the insole portion according to a shape of the orthotic shell.

19. A method for manufacturing an orthotic footwear, the method comprising:
forming a flat sole from an insole portion and an outsole portion;
forming a concave region from a layer of semi-rigid material that is configured to support a heel region of a foot of a person; and
forming a convex region from the layer of semi-rigid material at an end of the concave region, the convex region being configured to support an arch region of the foot,
wherein the convex region is configured to deflect under a downward force applied thereon which increases a chord length of the convex region in a longitudinal direction such that the layer of semi-rigid material corresponding to the convex region becomes relatively flatter with the downward force causing the deflection of the convex region, and
wherein the increase in the chord length causes reactive rotation of the concave region toward the heel region of the foot causing the layer of semi-rigid material corresponding to the concave region to rotate toward the heel region of the foot such that a part of the flat sole rotates toward the heel region of the foot.

20. A method for providing dynamic orthotic support to a foot of a wearer by a sole of a footwear device fitted with a semi-rigid orthotic shell, the semi-rigid orthotic shell having a rigidity that is greater than the sole, the orthotic shell comprising a heel portion and a midfoot portion, the method comprising:
inserting the foot into a strap connected to the footwear device such that the strap is on top the foot;
applying a downward force on the midfoot portion of the orthotic shell;
bending the midfoot portion in response to applying the downward force on the midfoot portion of the orthotic shell;
reactively rotating the heel portion of the orthotic shell towards the foot in response to the bending of the midfoot portion,
wherein the reactively rotating heel portion of the orthotic shell presses the sole against the foot to provide dynamic orthotic support to the foot of the wearer; and
lifting the foot such that the footwear device is free to dangle on top of the foot from the strap.

* * * * *